(12) United States Patent
Jepsen

(10) Patent No.: US 8,374,800 B2
(45) Date of Patent: Feb. 12, 2013

(54) DETERMINING PARAMETERS OF THE DIELECTRIC FUNCTION OF A SUBSTANCE IN AQUEOUS SOLUTION BY SELF-REFERENCED REFLECTION THZ SPECTROSCOPY

(75) Inventor: Peter Uhd Jepsen, Copenhagen (DK)

(73) Assignee: Danmarks Tekniske Universitet, Lyngby (DK)

( * ) Notice: Subject to any disclaimer, the term of this patent is extended or adjusted under 35 U.S.C. 154(b) by 502 days.

(21) Appl. No.: 12/305,612

(22) PCT Filed: Jul. 5, 2007

(86) PCT No.: PCT/DK2007/050083
§ 371 (c)(1),
(2), (4) Date: Jul. 29, 2010

(87) PCT Pub. No.: WO2008/003328
PCT Pub. Date: Jan. 10, 2008

(65) Prior Publication Data
US 2010/0292936 A1  Nov. 18, 2010

Related U.S. Application Data

(60) Provisional application No. 60/818,323, filed on Jul. 5, 2006.

(30) Foreign Application Priority Data

Jul. 5, 2006 (EP) .................................... 06116664

(51) Int. Cl.
*G06F 19/00* (2011.01)
*G01N 21/35* (2006.01)
(52) U.S. Cl. .............................. 702/25; 356/51; 356/517

(58) Field of Classification Search .................... 702/25; 356/300–334, 51, 517; 250/339.07
See application file for complete search history.

(56) References Cited

U.S. PATENT DOCUMENTS 5,922,609 A   7/1999  Kellner et al.
7,601,977 B2 * 10/2009 Yeh et al. .................. 250/504 R

FOREIGN PATENT DOCUMENTS

DE   103 09 845 A1   9/2004
EP   1 548 426 A1   6/2005

(Continued)

OTHER PUBLICATIONS

E.R. Brown, et al., "Coherent millimeter-wave generation by heterodyne conversion in low-temperature-grown GaAs photoconductors" J. Appl. Phys., Feb. 1, 1993, pp. 1480-1484, vol. 73.

(Continued)

*Primary Examiner* — Sujoy Kundu
(74) *Attorney, Agent, or Firm* — Knobbe Martens Olson & Bear LLP

(57) ABSTRACT

Method and apparatus for determining dielectric function of liquid solutions and thereby concentrations of substances in aqueous solution or the volatile/non-volatile nature of the liquid by self-referenced reflection THz spectroscopy. Having the aqueous solution in any container with a window allows irradiating coherent THz radiation with frequencies within the range 0.05-2 THz on the front of the window, and recording both a reference signal reflected from the front of the window and a sample signal reflected from the back of the window in contact with the aqueous solution. From these signals, the complex index of refraction, (I) or the complex reflection coefficient (II), can be calculated. The calculated components are compared with previously determined components from samples with known concentrations, whereby a concentration of the substance in the mixture can be estimated. The invention is particularly useful for determining alcohol (ethanol) content in aqueous solution containing other substances and particles.

19 Claims, 13 Drawing Sheets

FOREIGN PATENT DOCUMENTS

| RU | 2 207 564 C2 | 6/2003 |
|---|---|---|
| WO | WO 2005/047873 A2 | 5/2005 |
| WO | WO 2005/119214 A1 | 12/2005 |

OTHER PUBLICATIONS

Adrian Dobroiu, et al., "Monolithic Fabry-Perot resonator for the measurement of optical constants in the terahertz range" Applied Physics Letters, 2005, vol. 86, 261107.

J. T. Kindt, et al., "Far-infared absorption spectra of water, ammonia, and chloroform calculated from instantaneous normal mode theory" J. Chem. Phys., Mar. 15, 1997, pp. 4389-4400, vol. 106, No. 11.

Hideaki Kitahara et al., "Dielectric Characteristics of Water Solutions of Ethanol in the Terahertz Region" Journal of the Korean Physical Society, Jan. 2005, pp. 82-85, vol. 46, No. 1.

K.A. McIntosh, et al., "Terahertz measurements of resonant planar antennas coupled to low-temperature-grown GaAs photomixers" Appl. Phys. Lett., Dec. 9, 1996, pp. 3632-3634, vol. 69, No. 24.

Cecilie Rønne "Intermolecular Liquid Dynamics Studied by THz-Spectroscopy" Ph.D. Thesis, The Faculty of Science Aarhus University, Oct. 2000, pp. 1-129.

Ronne, C. et al., "Investigation of the Temperature Dependence of Dielectric Relaxation in Liquid Water by THz Reflection Spectroscopy and Molecular Dynamics Simulation" J. Chem. Phys., vol. 107, No. 14, Oct. 8, 1997, pp. 5319-5331.

Thrane et al., "THz Reflection Spectroscopy of Liquid Water" Chemical Physics Letters, North-Holland, Amsterdam, vol. 240, No. 4, Jun. 30, 1995, pp. 330-333.

Arikawa, T. et al., "Dynamics of Biomolecules in Water by Terahertz Time-domain Attenuated Total Reflection Spectroscopy" Infrared and Millimeter Waves and 13th International Conference on Terahertz Electronics, 2005. IRMMW-THZ 2005. The Joint 30th International Conference on Williamsburg, VA., Sep. 19-23, 2005, Piscataway, NJ, pp. 52-53.

Tanabe, T., et al., "Attenuated Total Reflection Spectroscopy of Liquids Using GaP-Raman Terahertz Spectrometer" Infrared and Millimeter Waves and 13th International Conference on Terahertz Electronics, 2005. IRMMW-THZ 2005. The Joint 30th International Conference on Williamsburg, VA., Sep. 19-23, 2005, Piscataway, NJ, pp. 50-51.

Hirori, H., et al., "Attenuated Total Reflection Spectroscopy in Time Domain Using Terahertz Coherent Pulses" Japanese Journal of Applied Physics, vol. 43, No. 10a, 2004, pp. L1287-L1289.

Pedersen, J., et al., "THZ Time-Domain Spectroscopy of Nonpolar Liquids" Journal of Quantum Electronics, Service Center, Piscataway, NJ, vol. 28, No. 10, Oct. 1, 1992, pp. 2518-2522.

Zidmars, D. et al., "Terahertz Reflection Imaging for Package and Personnel Inspection" Proceedings of the Spie, Spie, Bellingham, VA, vol. 5411, No. 1, 2004, pp. 78-83.

International Search Report Dated Oct. 12, 2007 for PCT/DK2007/050083.

* cited by examiner

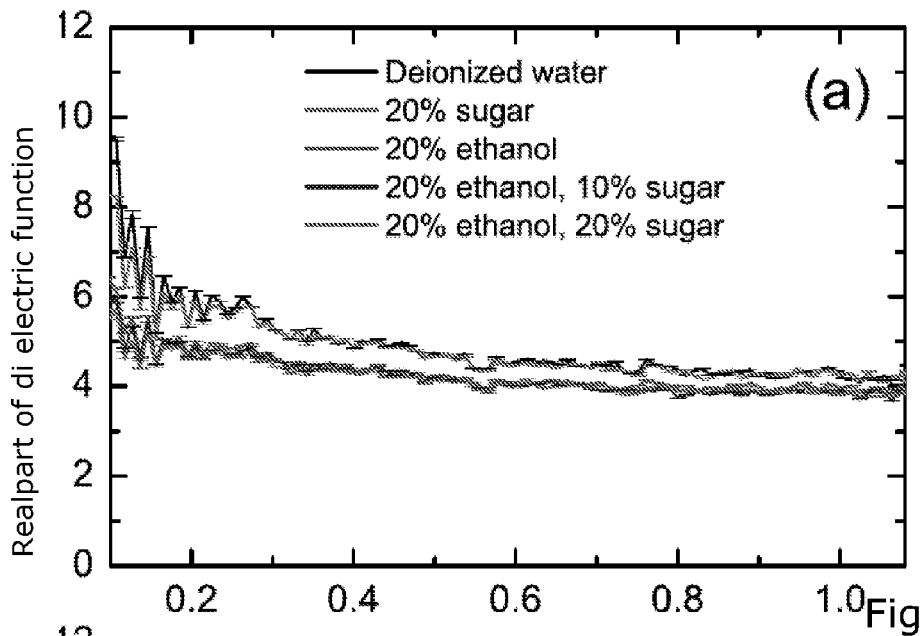
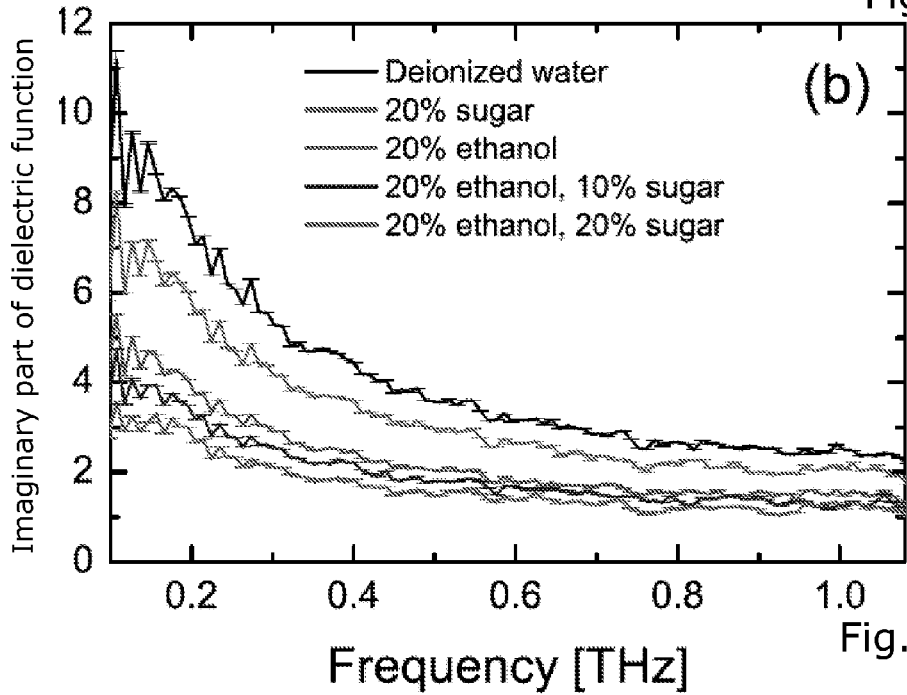
Fig. 13A
Fig. 13B

DETERMINING PARAMETERS OF THE DIELECTRIC FUNCTION OF A SUBSTANCE IN AQUEOUS SOLUTION BY SELF-REFERENCED REFLECTION THZ SPECTROSCOPY

CROSS REFERENCE TO RELATED APPLICATION

This application claims the benefit and priority to and is a U.S. National Phase of PCT International Application Number PCT/DK2007/050083, filed on Jul. 5, 2007, designating the United States of America and published in the English language, which is an International Application of and claims the benefit of priority to European Patent Application No. 06116664.1, filed on Jul. 5, 2006, and U.S. Provisional Application No. 60/818,323, filed On Jul. 5, 2006. The disclosures of the above-referenced applications are hereby expressly incorporated by reference in their entireties.

FIELD OF THE INVENTION

The present invention relates to the field of optically determining concentrations of substances in aqueous solution. More specifically, the invention relates to determining concentrations of substances in aqueous solution by self-referenced reflection THz spectroscopy.

BACKGROUND OF THE INVENTION

Present optical methods for determining concentrations of substances in aqueous solution are typically based on spectroscopic methods applying near-infrared (NIR) light, such as Fourier transform IR (FTIR) spectroscopy.

NIR light has the advantage that many substances have a characteristic fingerprint in this spectral range, thereby allowing a precise identification of substances. However, this advantages turns into a disadvantage when more complicated mixtures comprising many substances and possibly suspended particles. Overlapping spectral fingerprints and/or the light scattering by particles makes is very difficult to perform quantitative estimates of the content of substances.

The dielectric characteristics of aqueous solutions in the THz range have been studied in e.g.:

Hideaki Kitahara et al, "Dielectric characteristics of water solutions of ethanol in the terahertz region", J. Korean Phys. Soc. 46, 82-85 (2005). This paper presents the THz spectrum of water-ethanol mixtures, measured in a transmission setup.

A. Dobroiu et al, "Monolithic Fabry-Perot resonator for the measurement of optical constants in the terahertz range", Appl. Phys. Lett. 86, 261107 (2005). This paper describes how a prism with one facet being used in total internal reflection (TIR) geometry forms a THz Fabry-Perot resonator. A factor T is introduced as a correction factor in an expression for relative amplitudes of consecutive harmonics of the resonator. The factor T expresses the increased loss when a liquid sample is provided on the TIR facet. By measuring the difference in relative amplitudes of consecutive harmonics with and without sample, T can be measured. Comparing the obtained T-values with T-values obtained for samples with known concentrations of a substance allows estimation of a concentration in an unknown sample. The T-value is inherently a mean value over a narrow frequency range, and does not contain spectral information.

However, most mixtures of industrial interest, e.g. in the foodstuff industry, does not consist of a single substance in pure water, but are rather complicated mixtures of many substances of different phases such as emulsions or suspended particles, bubbles etc. It is a disadvantage of prior art optical methods for determining concentrations of substances in aqueous solution that they are not adapted for use on such mixtures.

SUMMARY OF THE INVENTION

It is an object of the invention to provide a method and an apparatus for determining a concentration of a first substance in a water-based mixture with other substances. The method and an apparatus are adapted to determine concentrations even in opaque mixtures such as water-based emulsions and mixtures comprising suspended particles and/or dissolved and gaseous carbon dioxide.

To fulfil this object, the invention applies self referenced reflection THz spectroscopy combined with a chemometric data analysis. The THz spectroscopic measurements determines the behaviour of one or more dielectric properties of the mixture in the THz range, also referred to as a "dielectric THz trace" in the following. Typical dielectric properties or parameters of the dielectric function may be reflection coefficient, absorption coefficient, refractive index or similar. In a subsequent chemometric analysis, a determined dielectric THz trace is thereafter compared to previously determined traces for known concentrations of the first substance in water, and a concentration of the first substances in the mixture can be determined.

According to a first aspect, the invention provides a method for determining a concentration of a first substance in a liquid mixture containing water, the first substance and other substances, the method applies self-referenced reflection THz spectroscopy and comprises:

on a section of a plane window of thickness d and refractive index $n_{win}$ having a front and a back side, providing the mixture in contact with the back;

irradiating coherent THz radiation with frequencies within a range 0.05-2 THz on the front of the window section at an angle of incidence $\theta$, the incident radiation resulting in a reference signal reflected from the front of the window section and a sample signal reflected from the back of the window section;

recording the reference and sample signals in the time domain;

calculating at least one component of the complex index of refraction of the mixture $\hat{n}_{mix}(\omega)$ or the complex reflection coefficient $\hat{r}_{win/mix}(\omega)$, each of the at least one component being determined for at least two frequencies in said range; and comparing the calculated component(s) with a set of corresponding components being previously recorded and calculated for said at least two frequencies using the above steps on a set of samples with known concentrations of the first substance in water, thereby estimating a concentration of the first substance in the mixture.

A component (real or imaginary) of the complex index of refraction of the mixture $\hat{n}_{mix}(\omega)$ or the complex reflection coefficient $\hat{r}_{win/mix}(\omega)$ is what is referred to as a dielectric THz trace. Thus, each trace is a dielectric component calculated for a specific concentration for at least two frequencies such as for a continuous frequency range. Similarly, the set of corresponding components for said at least two frequencies are a set of dielectric THz traces. The "hat" ^ is used to indicate complex quantities.

According to a second aspect, the invention provides an apparatus for carrying out the method according to the first aspect. Thus, the second aspect provides an apparatus for optically determining a concentration of a substance in a liquid mixture containing water, the first substance and other substances, the apparatus comprising:

a reflection THz spectrometer comprising a source of THz radiation of frequency within a range 0.05-2 THz and a THz time domain detector;

a plane window section of thickness d and refractive index $n_{win}$ having a front and a back side, the back side being adapted to be in contact with the liquid mixture, the window section being positioned to receive THz radiation on the front of the window section at an angle of incidence $\theta$ from the source, and so that a reference signal being a reflection of the incident radiation on the front of the window section and a sample signal reflected being a reflection of the incident radiation on the back of the window section can be detected by the THz time domain detector;

a data processing unit comprising
means calculating at least one component of the complex index of refraction of the mixture, $\hat{n}_{mix}(\omega)$, or the complex reflection coefficient, $\hat{r}_{win/mix}(\omega)$, based on signals detected by the THz time domain detector, each of the at least one component being determined for at least two frequencies in said range;
storage means holding a set of corresponding components being previously recorded and calculated for said at least two frequencies using the above steps on a set of samples with known concentrations of the first substance in water,
means for comparing the calculated component(s) with the set of previously recorded corresponding components to estimate a concentration of the first substance in the mixture.

In reflection THz spectroscopy, dissolved substances typically have no characteristic fingerprint in the form of spectral peaks, but rather tend to affect the overall variation of the spectra, e.g. the inclination over the entire spectral range. This means that spectral features from other substances do not occupy the entire spectrum, which again means that determination can be made in even complicated mixtures. Also, it follows that measurement at a single wavelength will not provide sufficient information to make quantitative determinations for substances—rather, several determinations of the dielectric component over the THz range are needed.

Thus, it also follows that the more determinations of the component at different wavelengths the trace comprises, the better a basis for comparison with previously determined components and the more precise an estimate of the first substance concentration. THz radiation at different wavelengths may be generated by different scenarios, a large bandwidth scenario using broadband ultrashort pulses and a discrete frequencies scenario using tuneable continuous wave (CW) radiation. In both scenarios, it is preferred that the dielectric THz trace comprise a value in at least each of the following intervals (THz): [0.05; 0.25] and ]0.25; 0.8], or preferably in at least each of the following intervals: [0.05; 0.15], ]0.15; 0.4] and ]0.4; 1.5], where values in different intervals are preferably separated by at least 0.1 THz. Including frequencies in different intervals has the advantage that the spectral information is utilized, providing a much better estimate than prior art determinations based only on values at a single frequency (or within a very narrow frequency range). The broadband pulses preferably have a bandwidth covering at least 0.1-1 THz, but may preferably have a larger bandwidth, such as up to several THz, e.g. 10 THz, whereby even more spectral information may be extracted.

In the embodiment applying broadband THz pulses it is preferred that
the incident coherent THz radiation is broadband pulses, so that the reference and sample signals are corresponding pulses with corresponding bandwidths;
the step of recording the reference and sample signals comprises recording the signal strength of the reference and sample pulses, $\hat{E}_{ref}(t)$ and $\hat{E}_{sam}(t)$, and determining a difference in arrival time between reference and sample pulses originating from the same incident pulse; and that
the step of calculating at least one component comprises determining a relative amplitude of and a phase shift between the reference and sample signals in the frequency domain, $$\frac{\hat{E}_{sam}(\omega)}{\hat{E}_{ref}(\omega)} = A_m^{new} \exp(i\Delta_m^{new}).$$

Hence, time-domain spectra of the reflected pulses are recorded and preferably Fourier transformed to yield the relative amplitude of and a phase shift in the frequency domain. These values are applied in a following mathematical analysis to be described in detail later. As a result of this analysis, the step of calculating at least one component of $\hat{n}_{mix}(\omega)$ or $\hat{r}_{win/mix}(\omega)$ preferably applies an expression of the form $$\hat{r}_{win/mix}(\omega) = \frac{A_m^{new}}{A_m^{ref}} r_{win/air} \exp(i(\Delta_m^{new} - \Delta_m^{ref}))$$

or $$\hat{n}_{mix}(\omega) = \frac{\sqrt{n_{win}^2(1-\hat{r}_{win/mix})^2 + 4\hat{r}_{win/mix}\sin^2\theta}}{1+\hat{r}_{win/mix}},$$

where $A_m^{ref}$ and $\Delta_m^{ref}$ are relative amplitude and phase measured previously measured without air on the back of the window section and $r_{win/air}$ is the reflection coefficient with air on the back of the window section.

The previously measured relative amplitude and phase, $A_m^{ref}$ and $\Delta_m^{ref}$, are preferably determined only once for each combination of d, $n_{win}$ and $\theta$, by performing the above steps without a mixture in contact with the back of the window section. This provides the advantage that no reference cell or a reference measurement is needed once the THz reflection arrangement is set up and aligned. Hence, the method can determine concentrations in setups where it is not practical to record reference spectra without samples, such as for flowing liquids or tanks or vessels.

In the embodiment applying single frequency THz radiation, it is preferred that
the incident coherent THz radiation comprises two or more discrete (CW) frequencies within a range of 0.1-1.5 THz, so that the reference and sample signals forms an interference signal;
the step of recording the reference and sample signals comprises recording, for each of the two or more discrete frequencies, an amplitude and a phase of said interference signal, $A_i^{new} \exp(i\Delta_i^{new}) = \hat{E}_{sam}(\omega) + \hat{E}_{ref}(\omega)$; and
the step of calculating at least one component comprises determining a difference between said interference signal and a similar interference signal previously recorded without a mixture in contact with the back of the window section.

To obtain the largest sensitivity, it is further preferred that the two or more discrete frequencies are selected to substantially coincide with a frequency where said interference signal have a minimum or a maximum.

As previously mentioned, the mixture may be opaque in that some of the other substances scatters visible and NIR light, opaque mixtures may be a water-based emulsion (e.g. milk, one other substances being fat globules), may comprise suspended particles (e.g. products in a fermentation process, one other substances being yeast particles), or may comprise dissolved and gaseous carbon dioxide (e.g. beer, soda or sparkly wine, the other substances being $CO_2$ bubbles). Typical sizes of individual globules of fat in e.g. milk ranges from 0.5 to 10 micron in diameter. For opaque mixtures, the invention provides the advantages that the dielectric THz trace is not influenced by particles and fluid globules. This is in part due to that only a reflection at a window/mixture is measures so that no transmission through the mixture is required, and in part due to the large wavelength of THz radiation.

The set of previously determined components are the dielectric component corresponding to the one determined for different frequencies in the dielectric THz trace. The set is determined on a set of known samples with known concentrations of the first substance in water. These known samples may:

resemble the composition of the mixture but for varying concentration of the first (and the second) substance, i.e. the content of the other substances are similar as for the mixture;

be solutions of the first (and the second) substance in pure water, i.e. no other substances;

be solutions of the first (and the second) substance and other substances in water, but with a different composition of the other substances than in the mixture.

Preferably, the first (and any second) substance is one of: alcohols such as methanol, ethanol or propanol, acetone, sugars such as sucrose, glucose or fructose, acids, fatty acids, salts, urea. Also, the other substances in the mixture preferably comprise one or more of: sugars, yeasts, fermentative products, colours, gaseous carbon dioxide, suspended particles, and fat globules.

How close the concentrations in the set of known samples should be depends on the desired precision, the chemometric prediction model, and the variation of the determined dielectric component as a function of the concentration. In a preferred implementation, the set of known samples has concentrations separated by intervals of approximately 1%. Throughout the present text, concentrations given in % are either % volume or % weight depending on the phase of the substance under standard conditions (% Vol for fluid substances and % Weight for dissolved solid substances). The skilled person will recognize that an ethanol concentration will typically be given in % Vol, whereas a concentration of sugar dissolved in a liquid is typically given in % Weight.

Traces for more than one component may be determined and compared to increase the precision, e.g., both an absorption coefficient and reflection coefficient may be determined.

The present invention provides the further advantage that it is practically independent on the available amount of mixture. Due to the reflection geometry, only a very thin layer of the mixture is needed on the window. The evanescent THz fields is completely absorbed after approximately 100 μm, hence by focusing the THz radiation to a spot size of 3 mm diameter and using a mixture layer of just above 100 μm, concentrations in samples as small as approximately 10 nanoliters may be determined. Thus, it may be preferred that the volume of mixture provided at the back of the window section is less than 1 μL, such as less than 0.1 μL, such as less than 20 nL.

In the other extreme, again due to the reflection geometry, the method may be applied to extremely large samples, e.g. by incorporating the window section in a large tank or vessel, such as a fermenting tank.

It is another advantage that the method according to the invention is self-referenced and applicable at all incidence angles and for all polarizations of the incident terahertz radiation. The method thereby provides a general method for the determination of the dielectric properties of liquids in environments where transmission measurements are difficult. Also, the method may be used on liquids contained behind different materials, such as glass or plastic.

In a preferred application, the method may simultaneously determine concentrations of more than one substance in the mixture. Here, other substances comprise a second substance and the samples with known concentrations have varying concentrations of said second substance. By comparing the calculated component(s) to the entire set of known samples and identifying the most similar trace, a concentration of both the first and the second substance in the mixture may be estimated. Preliminary measurements have shown that this application is especially suited for determining concentrations of sugars and alcohols in mixtures comprising sugars with a concentration in the interval 5-60% and alcohols with a concentration in the interval 5-90%.

In another aspect, the invention can be used to determine the volatile/non-volatile nature of liquids by self-referenced reflection THz spectroscopy as in the previous aspects. A more detailed description of the physical chemistry behind this mechanism will be given later in relation to a specific example.

Such method may be used to detect flammable liquids in sealed plastic containers, e.g. PET bottles used for carbonated and still softdrinks. Potential applications may be for security checks in airports, public events such as football games, or access control to secured building such as governmental buildings. Another application may be for automatic sorting of return bottles in recycle plants where flammable liquids could cause explosions.

In this aspect, the invention provides a method for detecting volatile liquids in closed containers, the method applies self-referenced reflection THz spectroscopy and comprises:

providing a container holding a liquid, a section of the container being transparent to THz electromagnetic radiation, having thickness d and refractive index $n_{win}$ and a front and a back side, where the liquid is in contact with the back side:

irradiating coherent THz radiation with frequencies within the range 0.05-2 THz on the front of the window section at an angle of incidence θ, the incident radiation resulting in a reference signal reflected from the front of the window section and a sample signal reflected from the back side of the window section;

recording the reference and sample signals in the time domain;

analysing at least the sample signal reflected from the back side of the window section to determine if the liquid is potentially volatile.

The analysis of the sample signal may be carried out on several levels of detail depending on the application and how critical a false positive detection would be. An embodiment of a relatively simple analysis may be to compare the signal strength and/or shape to previously recorded signals from known liquids. It the signal resembles that of a known volatile liquid, the measured liquid is potentially volatile and thereby potentially flammable.

In another embodiment providing more detailed knowledge of the liquids, the method may further comprise:
- calculating at least one component of the complex index of refraction of the mixture $\hat{n}_{mix}(\omega)$ or the complex reflection coefficient $\hat{r}_{win/mix}(\omega)$, each of the at least one component being determined for at least two frequencies in said range; and
- comparing the calculated component(s) to a predetermined threshold value to determine if the liquid is potentially volatile.

Here, a threshold value of e.g. a permittivity or a reflection coefficient or another dielectric function may be set, above or below which the liquid is deemed volatile.

In yet another embodiment providing even more detailed knowledge of the liquids, the step of comparing the calculated component(s) comprises comparing the calculated component(s) with a set of corresponding components being previously recorded and calculated for said at least two frequencies using the above steps on a set of volatile liquid samples, thereby estimating a degree of hydrogen-bonding of the liquid.

As will be described later, the method and apparatus according to the invention may perform the comparing and estimating by multivariate analysis.

BRIEF DESCRIPTION OF THE FIGURES

FIGS. 13A-B shows the real and imaginary part of the dielectric function of pure water, a 20% sucrose solution, a 20% ethanol solution, and two solutions containing 10 and 20% sucrose and 20% ethanol.

DETAILED DESCRIPTION OF THE INVENTION

Figure 1:
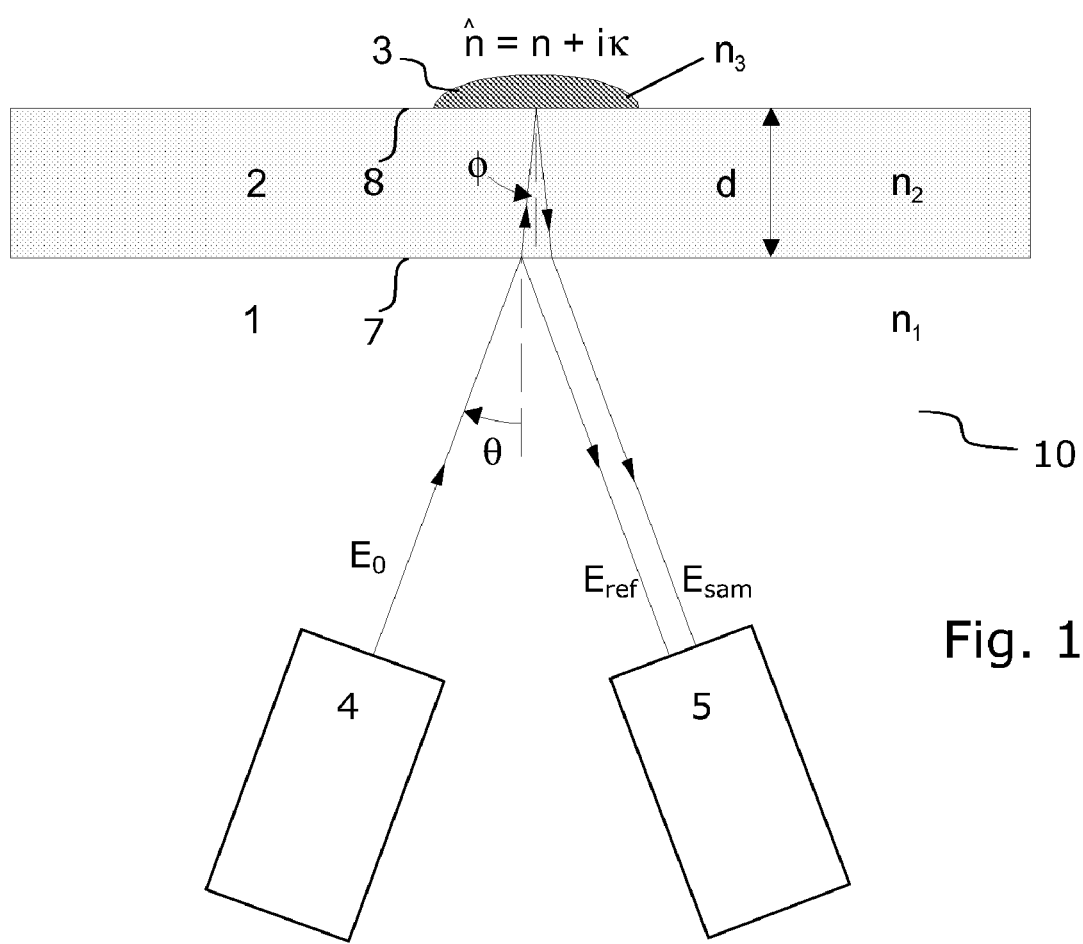
FIG. 1 illustrates the basic setup of reflection THz spectroscopy according to the invention.

In a preferred embodiment, the invention applies a self references THz reflection spectrometry arrangement 10 illustrated in FIG. 1. Here, a broadband or a tuneable THz source 4 generates THz beam $E_0$ incident on front facet 7 of a window section 2 under angle θ. The reflection of $E_0$ at front facet 7 generates a reference beam $E_{ref}$ depending on the reflection coefficient $r_{air/win}$. The transmitted part of $E_0$ is refracted and is incident on back facet 8 under angle φ. The reflection of $E_0$ at back facet 7 generates a sample beam $E_{sam}$ depending on the reflection coefficient $r_{win/sam}$ which again depends on the dielectric characteristics of sample 3 provided on the back facet of the window section. Signals $E_{sam}$ and $E_{ref}$ are recorded by time-domain spectrometer 5.

In the following, the analysis enabling calculating components of the complex index of refraction of the mixture $\hat{n}_{mix}(\omega)$ or the complex reflection coefficient $\hat{r}_{win/mix}(\omega)$ from the reflection terahertz spectroscopy measurements according to the method of the invention is presented. Reflection terahertz spectroscopy can be carried out in several ways; the present description provides the following two embodiments:

1. Reflection THz-TDS applying broadband pulses and using the arrangement illustrated in FIG. 1 with the front surface of a thick, transparent, high-index window as reference reflection plane and the back surface of the same window as the sample reflection plane.
2. Phase-sensitive single-frequency THz reflection measurements using the same arrangement of a high-index window as above, but here relying on amplitude-and phase variations at single frequencies.

For each embodiment of the method, the details of the steps of recording, calculating, comparing and estimating according to the invention can be extracted from the provided analysis and following examples by the person skilled in the art.

THz-TDS Applying Broadband Pulses

Figure 2:
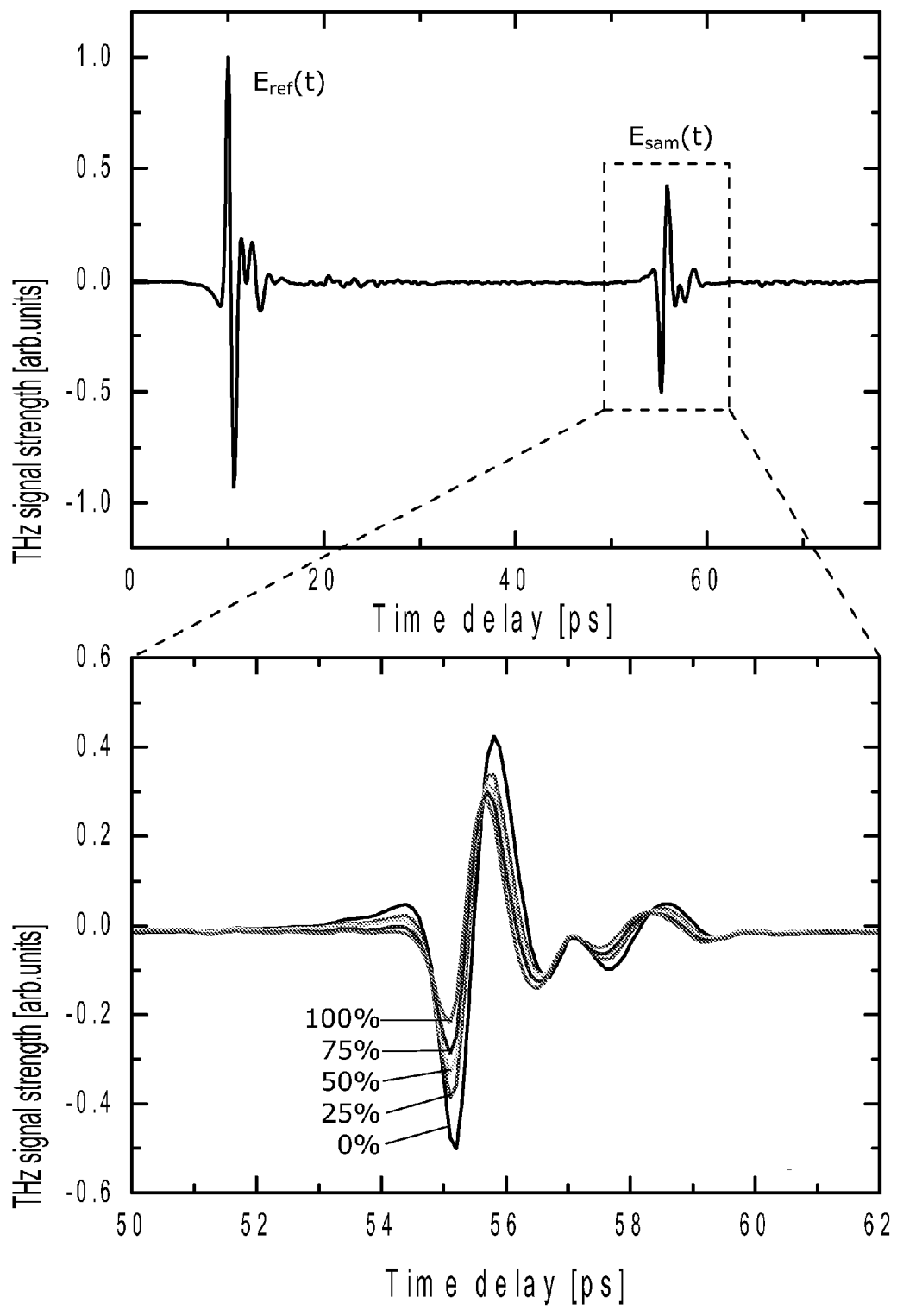
FIG. 2 shows a recorded time-domain spectrum with the reference signal $E_{ref}$ and the sample signal $E_{sam}$ in the embodiment applying broadband pulses.

Generating and detecting broadband THz pulses are standard techniques developed in the 1990's. Present day techniques build on the same principles, albeit applying developments in the field such as small and simple turn-key femtosecond lasers systems. In short, broadband THz pulses are generated by irradiating a THz emitting antenna with ultrashort (typically femtosecond) laser pulses. The THz emitting antenna is typically a metal-semiconductor-metal structure with two biased, metal striplines forming a photo-conductive switch. Thus, in this embodiment, the THz source 4 in FIG. 1 typically comprises a femtosecond laser system and a THz emitting antenna. THz pulses are detected using a THz detecting antenna with a similar design, except for a dipolar layout of the metal strips. When a laser pulse coincides spatially and temporally with the THz pulse, a photocurrent is induced. A delay line is used to scan a femtoseond laser pulse temporally, and the photocurrent is measured for each delay, resulting in a time-domain spectrum as shown in FIG. 2. Thus, in this embodiment, the THz spectrometer 5 in FIG. 1 typically comprises a THz detecting antenna, a delay line, an amp-meter and controlling and recording systems and software.

THz reflection spectrometry has been applied previously in e.g.:

L. Thrane et al, "THz reflection spectroscopy of liquid water", Chem. Phys. Lett. 230, 330-333 (1995). This paper contains the absorption spectrum of pure liquid water, and describes a simple version of THz reflection spectroscopy similar to the technique used in an embodiment of the present invention.

C. Rønne et al, "Investigation of the temperature dependence of dielectric relaxation in liquid water by THz reflection spectroscopy and molecular dynamics simulation", J. Chem. Phys. 107, 5319-5331 (1997). This paper gives further information on the temperature dependence of the dielectric function of pure liquid water in the THz range, and offers details about the THz reflection spectrometer.

C. Rønne, "Intermolecular liquid dynamics studied by THz-spectroscopy", Ph.D. Thesis, Aarhus University (2000). This thesis offers further details about the THz reflection spectrometer and some basics of the mathematical analysis.

These references may provide further details of the THz reflection spectrometry arrangement 10 and are included by reference.

Geometric Analysis

The fundamental geometry of the self-referenced reflection THz-TDS arrangement illustrated in FIG. 1 is analysed in the following. The analysis carried out in the frequency domain, where it is understood that the raw data are recorded in the time domain, and consist of a single trace containing the reference reflection $E_{ref}(t)$ and the sample reflection signal $E_{sam}(t)$ as recorded by spectrometer 5. The two signals are separated in the time domain, and individually Fourier transformed to the frequency domain. The two signals are now named $E_{ref}(\omega)$ and $E_{sam}(\omega)$, where $\omega = 2\pi\nu$ is the frequency measured in radians per second.

It is assumed that the input signal is incident on the front surface of the window at an angle θ. Consequently the incidence angle φ on the second interface is $$\sin\theta = n_{Si}\sin\phi \quad (1)$$

The effective single-pass propagation distance $d_{eff}$ inside the window material is $$d_{eff} = \frac{d}{\cos\phi} = \frac{n_{Si}d_{Si}}{\sqrt{n_{Si}^2 - \sin^2\theta}}. \quad (2)$$

The basic quantity needed in the analysis is the ratio between the sample signal and the reference signal. This ratio can be expressed as $$\frac{E_{sam}(\omega)}{E_{ref}(\omega)} = \frac{t_{12}\hat{r}_{23}t_{21}}{r_{12}}\exp(2in_{Si}\omega d_{eff}/c). \quad (3)$$

The transmission-and reflection coefficients are dependent on the incidence angle, and the reflection coefficient $\hat{r}_{23}$ is complex if the material behind the window is absorbing. This is the normal case in the spectroscopic measurement. For purposes of calibration of the spectrometer and characterization of the window material itself the measurement can also be carried out without sample material behind the window. In that case the reflection coefficient $\hat{r}_{23}$ is a real-valued number. The transmission coefficients $t_{12}$ and $t_{21}$ as well as the reflection coefficient $r_{12}$ are always real-valued. Since the radiation must be coupled into the window material, only angles below the total internal reflection angle are considered in this analysis.

The various transmission-and reflection coefficients are $$t_{12} = \frac{2\cos\theta\sin\phi}{\sin(\theta+\phi)} = \frac{2\cos\theta}{\cos\theta + \sqrt{n_{Si}^2 - \sin^2\theta}}, \quad (4)$$

$$t_{21} = \frac{2\cos\phi\sin\theta}{\sin(\theta+\phi)} = \frac{2\sqrt{n_{Si}^2 - \sin^2\theta}}{\cos\theta + \sqrt{n_{Si}^2 - \sin^2\theta}},$$

$$r_{12} = \frac{\cos\theta - \sqrt{n_{Si}^2 - \sin^2\theta}}{\cos\theta + \sqrt{n_{Si}^2 - \sin^2\theta}},$$

$$r_{23,air} = \frac{\cos\phi - n_{Si}\sqrt{1 - n_{Si}^2\sin^2\phi}}{\cos\phi + n_{Si}\sqrt{1 - n_{Si}^2\sin^2\phi}} = \frac{\sqrt{n_{Si}^2 - \sin^2\theta} - \sqrt{1 - \sin^2\theta}}{\sqrt{n_{Si}^2 - \sin^2\theta} + \sqrt{1 - \sin^2\theta}},$$

$$\hat{r}_{23,sample} = \frac{\cos\phi - \sqrt{\hat{n}^2/n_{Si}^2 - \sin^2\phi}}{\cos\phi + \sqrt{\hat{n}^2/n_{Si}^2 - \sin^2\phi}} = \frac{\sqrt{n_{Si}^2 - \sin^2\theta} - \sqrt{\hat{n}^2 - \sin^2\theta}}{\sqrt{n_{Si}^2 - \sin^2\theta} + \sqrt{\hat{n}^2 - \sin^2\theta}}.$$

Characterization of the Window Material and Beam Displacement

Normally the window material has known dielectric properties. High-purity silicon (Si) has an index of refraction of 3.4244 at room temperature and negligible absorption. The high index of refraction is ideal for the purpose because it results in a reflection coefficient at normal incidence of −0.54. However, as will be described later, windows of other materials such as PET can be used as well.

The known dielectric properties of the window material can also be used to solve an important problem in the experimental geometry. As shown in FIG. 1, the reference beam and the sample beam are displaced with respect to each other after the window reflections. This is difficult to take into account in a strictly formal manner, but nevertheless the effect of the displacement can be described in a more empirical way, in a manner similar to the iterative method discussed in the Ph.D. thesis of C. Rønne. In contrast to the method described therein, the method outlined here requires no iterative steps.

With no sample attached to the back surface of the window the ratio of the complex sample-and reference signals is $$\frac{E_{sam}}{E_{ref}} = A_m^{ref} \exp(i\Delta_m^{ref}) = \frac{t_{12} r_{23,air} t_{21}}{t_{12}} \exp(2(in)_{Si} d_{eff} \omega/c) A \exp(i\Delta). \quad (5)$$

Here the complex correction factor $A \exp(i\Delta)$ summarizes the complicated effects of the displacement of the sample beam with respect to the reference beam. The measured amplitude ratio and phase difference between the reference and the sample beams in this reference measurement are denoted $A_m^{ref}$ and $\Delta_m^{ref}$. The idea behind this is to adjust the amplitude and phase of the sample signal in such a way that the analysis results in the correct index of the window material. In the subsequent analysis of the signal from the spectroscopic measurement with a sample attached to the back side of the window this correction factor is assumed to be the same as without sample attached to the window.

Some algebraic manipulation leads to expressions for the amplitude A and phase $\Delta$ of the complex correction factor, $$A = A_m^{ref} \cdot \frac{r_{12}}{t_{12} r_{23,air} t_{21}} = A_m^{ref} \cdot \frac{\left(\cos\theta + \sqrt{n_{Si}^2 - \sin^2\theta}\right)^2}{4\cos\theta\sqrt{n_{Si}^2 - \sin^2\theta}}, \quad (6)$$

$$\Delta = \Delta_m^{ref} - \frac{2n_{Si} d_{eff} \omega}{c} - \pi.$$

These values can be stored for use in the analysis of spectroscopic measurements using the same experimental geometry (i.e. the same incidence angle, window thickness, and index of refraction). This indicates that it is required to measure $A_m^{ref}$ and $\Delta_m^{ref}$ every time the THz beam path is aligned, or the position of the reflection unit in the THz beam path is altered.

If the amplitude and phase of the actual spectroscopic measurement with a sample attached to the window back surface are denoted $A_m^{new}$ and $\Delta_m^{new}$, respectively, then the quantities used in the subsequent analysis should be $$A_m^* = \frac{A_m^{new}}{A} = \frac{A_m^{new}}{A_m^{ref}} \cdot \frac{t_{12} r_{23,air} t_{21}}{r_{12}}, \quad (7)$$

$$\Delta_m^* = \Delta_m^{new} - \Delta.$$

Extraction of the Dielectric Function of the Sample

Based on the results of the previous section it is now assumed that primary experimental data are available, and that the correction factor taking the displacement of the sample beam with respect to the reference beam has been taken into account already. If this is the case then Eq. (3) can be written as $$A_m^* \exp(i\Delta_m^*) = \hat{r}_{23,sample} \frac{t_{12} t_{21}}{r_{12}} \exp(2(in)_{Si} d_{eff} \omega/c). \quad (8)$$

Since the complex reflection coefficient $\hat{r}_{23,sample}$ contains the dielectric function of the sample material the following relation is useful, $$\hat{r}_{23,sample} = A_m^* \exp(i\Delta_m^*) \cdot \frac{r_{12}}{t_{12} t_{21}} \exp(-2(in)_{Si} d_{eff} \omega/c). \quad (9)$$

Reinserting the expression for $A_m^*$ and $\Delta_m^*$ results in an expression containing only the raw experimental data from the new measurement and from the reference measurement without the sample attached to the back surface of the window, $$r_{23,sample} = \frac{A_m^{new}}{A_m^{ref}} \cdot r_{23,air} \exp(i(\Delta_m^{new} - \Delta_m^{ref})) \quad (10)$$

$$= \frac{A_m^{new}}{A_m^{ref}} \cdot \frac{\sqrt{n_{Si}^2 - \sin^2\theta} - \sqrt{1 - \sin^2\theta}}{\sqrt{n_{Si}^2 - \sin^2\theta} + \sqrt{1 - \sin^2\theta}} \cdot \exp(i(\Delta_m^{new} - \Delta_m^{ref})).$$

Using Eq. (9) to find the expression for the complex index of refraction $\hat{n}$ of the sample results in $$\hat{n} = \frac{\sqrt{n_{Si}^2 (1 - \hat{r}_{23,sample})^2 + 4\hat{r}_{23,sample} \sin^2\theta}}{1 + \hat{r}_{23,sample}} \quad (11)$$

It thus follows, that having determined the relative amplitude of and a phase shift between the reference and sample signals in the frequency domain, $$\frac{\hat{E}_{sam}(\omega)}{\hat{E}_{ref}(\omega)} = A_m^{new} \exp(i\Delta_m^{new}),$$

one or more dielectric THz traces can be calculated.

The set of previously recorded components can thereby be determined using a set of known samples with known concentrations. Similarly, the components for the first (and the second) substance can be determined and compared with the set to estimate a concentration.

In the embodiment described in the following, the THz source 4 and THz detector of FIG. 1 is described in the following. Generation of coherent THz radiation at a single frequency is carried out with a laser source containing two discrete frequencies $\omega_1$ and $\omega_2$, typically from a commercially available tunable laser system. These two frequencies are combined in a photoconductive switch, typically fabricated on low-temperature-grown GaAs or another material with ultrafast carrier lifetime and an electronic band gap suited for the laser excitation wavelength. If the difference frequency is lower than the inverse lifetime of photogenerated carriers in the semiconductor material, $|\omega_1 - \omega_2| < 1/\tau$, then the carrier concentration in the photoconductive switch will be modulated at the difference frequency. An applied bias will then result in a sinusoidally varying photocurrent, leading to emission of a sinusoidally varying electric field if the photoconductive switch is attached to an appropriate antenna structure.

The generated radiation will propagate in free space, and can be focused and guided much like ordinary optical beams. The limitation is the diffraction limit, like in the case of broadband THz radiation. Reflection, transmission and interference of the beam will lead to amplitude-and phase changes of the signal. In the special case where the signal is reflected off a partially transparent window material, such as a planeparallel silicon window, the reflected light will be the superposition of the partial wave reflected from the front surface and the partial wave reflected from the back surface (in contact with the sample material) of the window.

Changes of the phase and/or amplitude of the reflection coefficient of the back surface will lead to changes in the interference between the two partial waves. This change will be related to the dielectric properties of the material in contact with the back side of the window. The window thickness can be chosen so that there is destructive interference of the two partial waves. Hence the combined signal will be very small. A small change in the dielectric properties of the material behind the window will then lead to a large relative change in the reflected signal.

The coherent detection of the single-frequency THz radiation is carried out in a photomixer structure similar to the structure used for emission of the radiation. THz radiation is captured by a suitable, resonant antenna structure on a semiconductor substrate. The electric field will be guided to a photoconductive gap. Now a fraction of the two-frequency laser field is focused in the photoconductive gap. The resulting modulation of the carrier concentration at the difference frequency will lead to a photocurrent in the attached circuitry if the THz field is in phase with the carrier concentration modulation. If, in contrast, the carrier concentration modulation and the THz field are 90 degrees out of phase, no photocurrent will be detected since both charge carriers and an electric field must be present at the same time in order to draw a photocurrent. Hence by scanning the temporal delay, or phase, of the laser beams incident on the detector with respect to the phase of the THz wave while measuring the photocurrent, a signal containing both amplitude and phase of the THz signal can be recorded.

Further details of the generation and detection of single frequency THz radiation may be found in Brown et al, Journal of Applied Physics 73, 1480-1484 (1993) or McIntosh et al, Applied Physics Letters 69, 3632-3634 (1996).

Extension of this technique to two or more single frequencies requires either control of one of the two laser frequencies, or more discrete frequencies in the laser beam. With a frequency-tunable laser it is possible to perform frequency sweeps of the THz radiation.

Extraction of Dielectric Properties from Single-Frequency Measurements

If a single-frequency electromagnetic wave is incident on a plane window, the reflected wave will be the coherent superposition of all the partial waves resulting from multiple internal reflections within the window. In the broadband measurements discussed in the previous section the inclusion of multiple reflections of the THz signal inside the window material could be avoided because of the temporal separation of the reference-and sample signals. In the case of single-frequency radiation this is not possible. Hence all internal reflections must be taken into account. In this situation the expression for the reflected field is $$\hat{E}_1 = \sum_{n=0}^{\infty} \hat{E}_1^{(n)} = \hat{E}_0 r_{12} + \hat{E}_0 t_{12} \hat{t}_w \hat{r}_{23} t_{21} + \hat{E}_0 t_{12} \hat{t}_w \hat{r}_{23} r_{21} \hat{t}_w \hat{r}_{23} t_{21} + \ldots$$
$$= \hat{E}_0 \left( r_{12} + t_{12} t_{21} \hat{r}_{23} \sum_{n=0}^{\infty} (\hat{t}_w r_{21} \hat{r}_{23})^n \right) \quad (12)$$

$$= \hat{E}_0 \left( r_{12} + \frac{t_{12} t_{21} \hat{r}_{23}}{1 - \hat{t}_w r_{21} \hat{r}_{23}} \right),$$

where $\hat{t}_w = \exp(2 i n_{Si} d_{eff} \omega/c)$ is the propagation function through the window material (assuming no losses), and $t_{12}$, $t_{21}, r_{12}, r_{21}, \hat{r}_{23}$ are the transmission-and reflection coefficients defined in Eq. (4), and $\hat{E}_0$ and $\hat{E}_1$ are the incident and reflected fields, respectively.

A change in the amplitude and phase of the reflection coefficient $\hat{r}_{23}$ of the window-sample interface will lead to a change in the amplitude and phase of the reflected electric field.

Figure 3A:
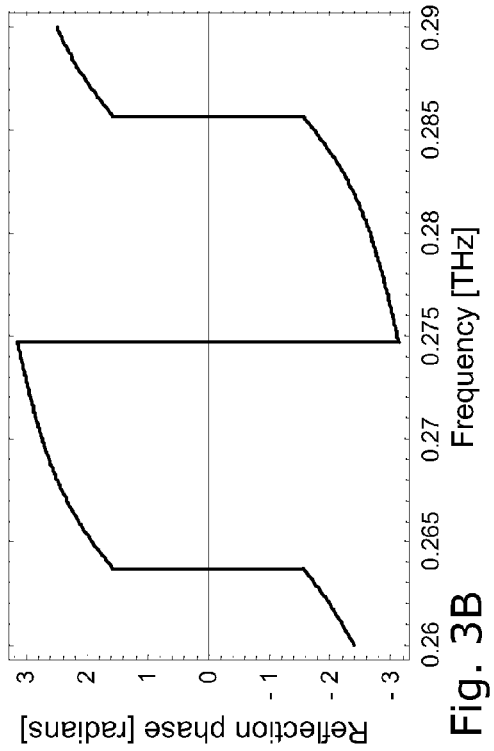
FIGS. 3A and B show amplitude (3A) and phase (3B) spectra of a calculated interference signal between the reference signal $E_{ref}$ and the sample signal $E_{sam}$ in the embodiment applying single-frequency measurements.
Figure 3B:
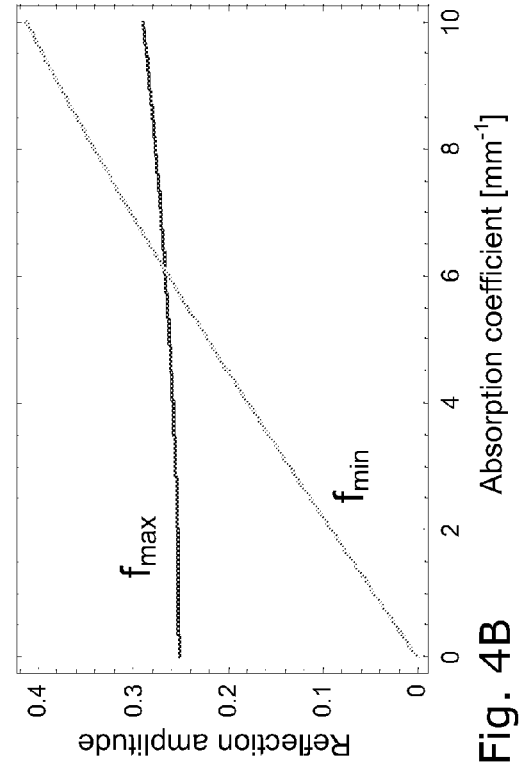

Based on the result in Eq. (12), the amplitude and phase of the frequency spectrum of the reflection coefficient in a narrow range between 0.26 and 0.29 THz is shown in FIGS. 3A and B. These show calculated amplitude (3A) and phase (3B) of the reflection coefficient as function of frequency for a window of thickness d=2.0 mm. The Fabry-Perot interference fringes are dominant in the reflection spectrum. Clear minima and maxima in the reflection coefficient are seen, these are the result of destructive and constructive interference between the partial waves in the window material. We will concentrate on the situations where the frequency is adjusted either to the minimum at 0.264 THz or to the maximum near 0.275 THz. In the following we will consider changes of the reflection coefficient at the mimina and at the maxima, and determine the influence of changes in the index of refraction and absorption coefficient of the sample material placed in contact with the back side of the window.

Figure 4A:
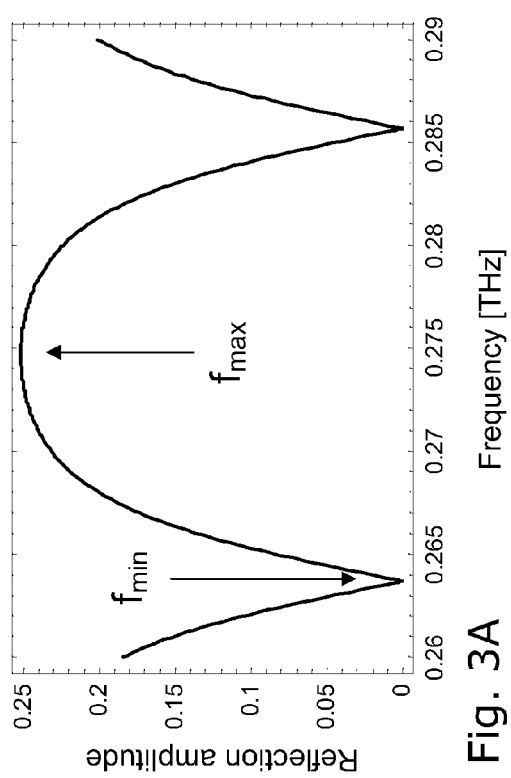
FIGS. 4A-B and 5A-B show calculated amplitude and phase of the interference signal of FIG. 3 as a function of index of refraction and absorption coefficient.
Figure 4B:
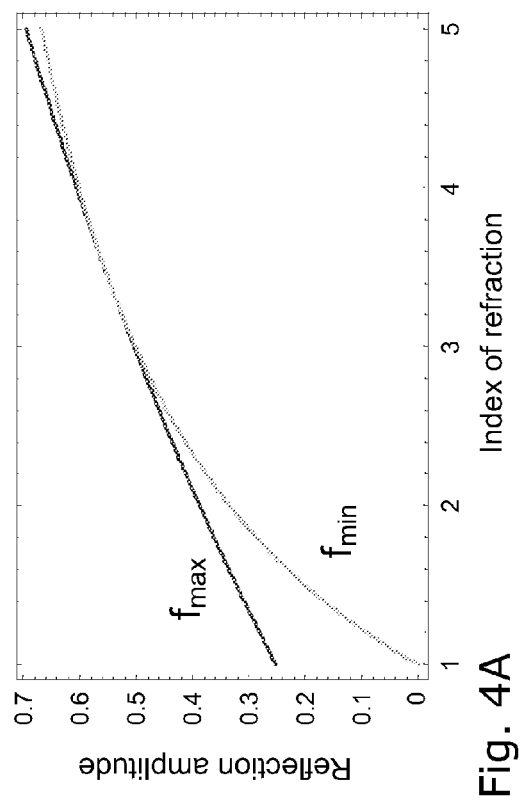

In FIGS. 4A and B, the amplitude of the reflection coefficient is plotted for a range of refractive indices and a range of absorption coefficients of the sample material. The figures show reflection amplitude as function of the index of refraction (4A) and absorption coefficient (4B) of the sample material. The $f_{max}$ curve is calculated with the frequency adjusted to the reflection maximum near 0.275 THz and the $f_{min}$ curve is calculated when the frequency is adjusted to the reflection minimum near 0.264 THz. The changes in the dielectric properties of the sample material are clearly seen as significant modification of the amplitude of the reflection coefficient, especially of the frequency is adjusted to a reflection minimum.

Figure 5A:
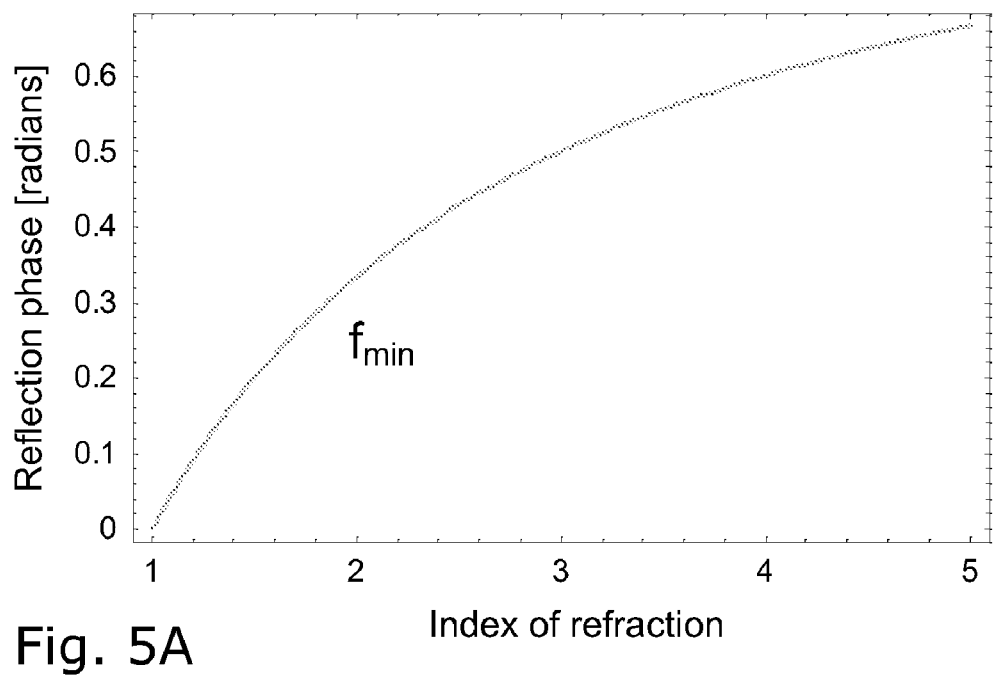
Figure 5B:
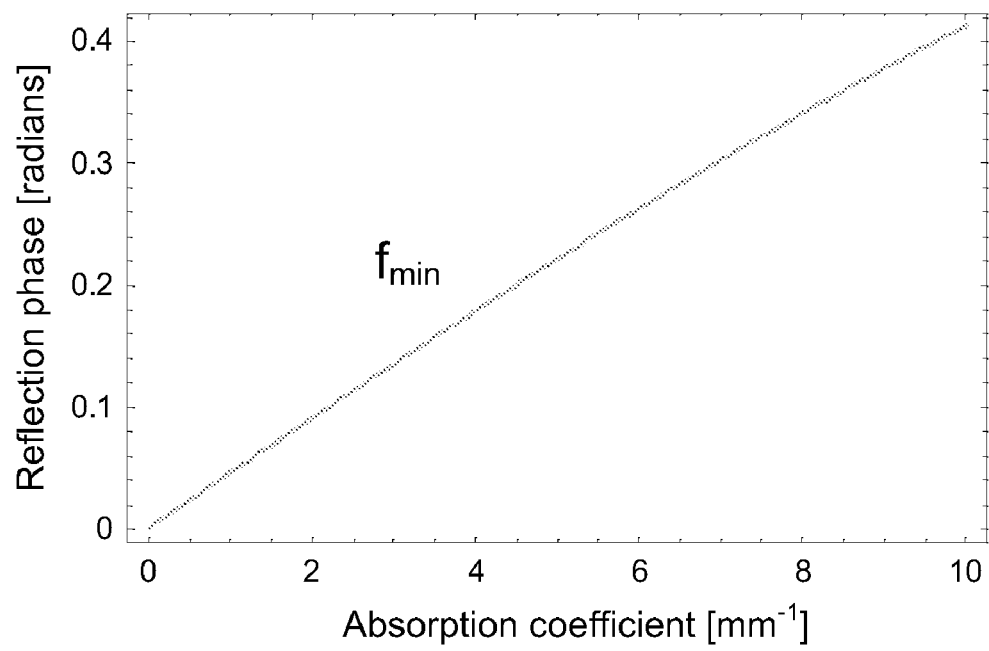

In FIGS. 5A and B, the phase of the reflection coefficient is plotted as function of a range of refractive indices (5A) and a range of absorption coefficients (5B) of the sample material in contact with the back side of the window. In this figure we concentrate on the situation where the frequency is adjusted to a reflection minimum since this is where the sensitivity seems to be largest. Similar, but somewhat smaller phase changes are observed at the reflection maximum, and a more detailed analysis will determine which detection strategy is best in terms of dynamic range and signal-to-noise ratio.

It thus follows, that having determined the reflected amplitude and/or phase, a value of a dielectric component (e.g. index of refraction or absorption coefficient) can be calculated. Performing this for two or more THz frequencies yields a dielectric THz trace. The set of previously recorded components can thereby be determined using a set of known samples with known concentrations. Similarly, the components for the first (and the second) substance can be determined and compared with the set to estimate a concentration.

EXAMPLES

In the following examples of recorded spectra, calculated dielectric THz traces and comparisons estimating substance concentrations will be given. The examples apply the broadband THz pulse embodiment described previously using the arrangement 10 described in relation to FIG. 1.

The examples have been recorded using a THz pulse duration of 1 ps and a bandwidth of 2 THz. The THz beam was focused to a frequency-independent spot diameter of 4 mm at the window interface 7. The window diameter was 50 mm, and its thickness d was 2 mm. The THz traces were recorded using a 2 mL volume of the mixture 3. The repetition rate of the femtosecond laser system driving the THz source 4 and THz spectrometer 5 was 88 MHz. The emitter 4 was biased with a modulated voltage at a frequency f=1.7 kHz. Each data point in the temporal traces was recorded with a lock-in amplifier operating with a time constant of 50 ms and locked to the modulation frequency f. The temporal traces were recorded with a step width of 100 femtoseconds.

FIG. 2 shows time-domain spectra recorded for samples 3 with different concentrations of water in a water-dioxane mixture. The reference pulse $E_{ref}(t)$ from the reflection on front facet 7 and the sample pulse $E_{sam}(t)$ from the reflection on back facet 8 are easily identified. As can be seen in the enlargement, the shape of $E_{sam}(t)$ is clearly dependent on the composition of the sample.

Figure 6A:
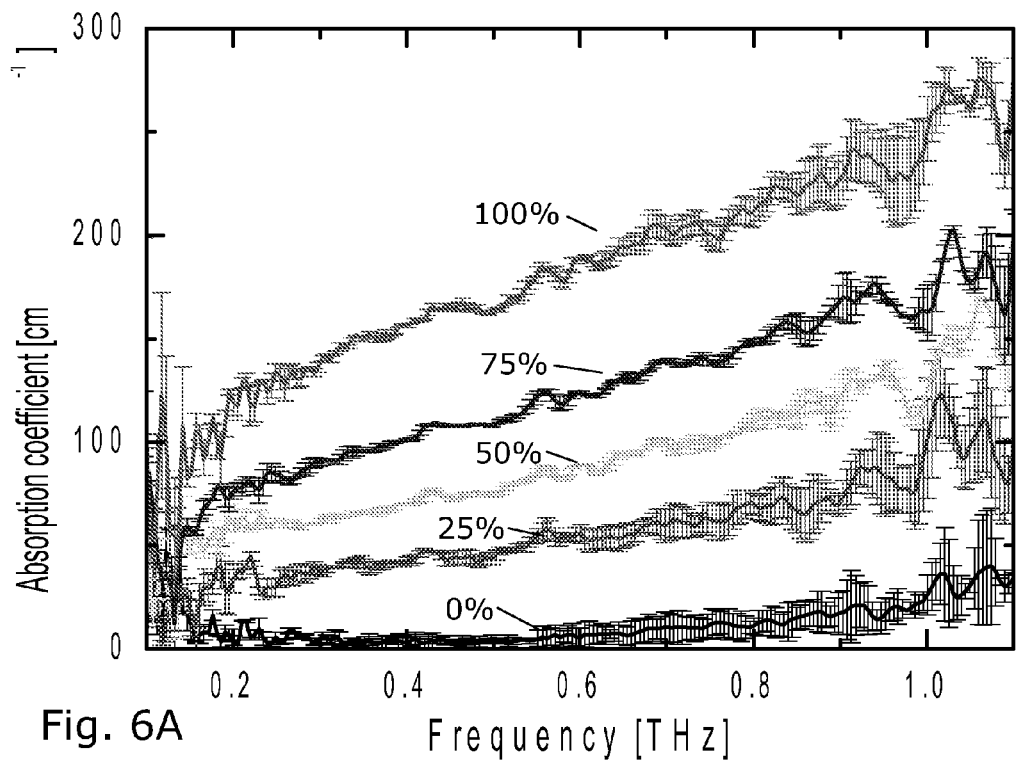
FIGS. 6A and B show dielectric THz traces, absorption coefficient (6A) and index of refraction (6B), of dioxane-water mixtures (% $H_2O$).
Figure 6B:
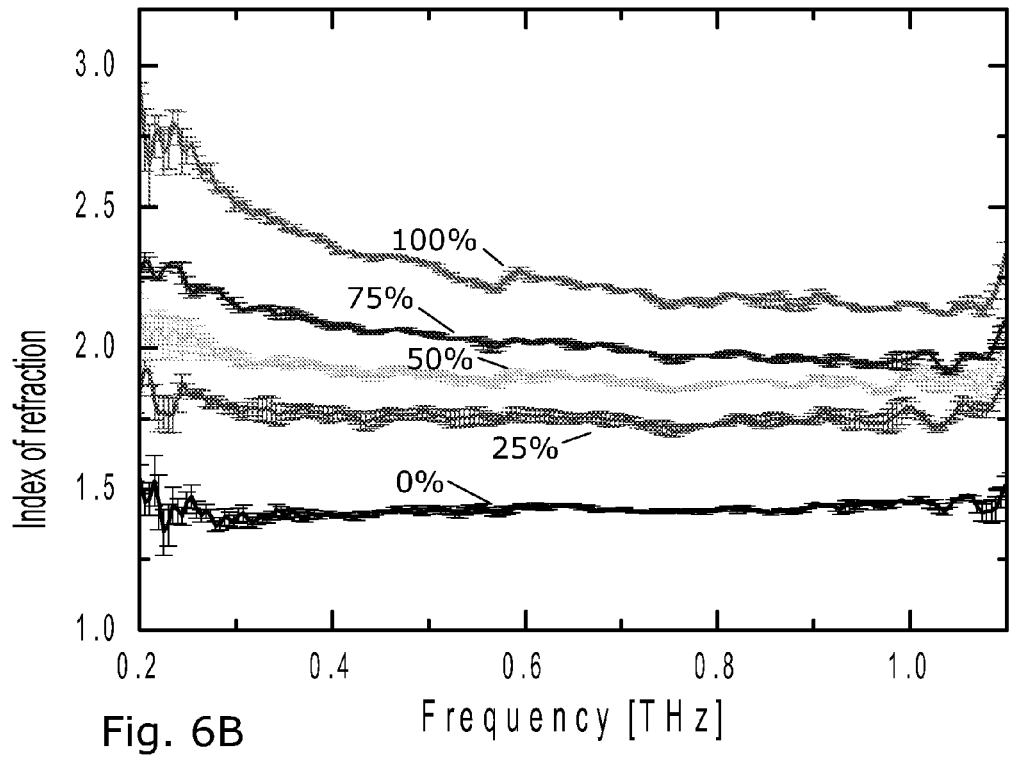

Applying the data analysis outlined in the above, especially Equations (10) and (11), two dielectric THz traces were calculated for each concentration; the absorption coefficient (imaginary part of complex refractive index) shown in FIG. 6A and the refractive index (real part of complex refractive index) shown in FIG. 6B. As can be seen, traces corresponding to different concentrations are very different in their overall behaviour (mean value, inclination) rather than in spectral fingerprints in the form of distinct peaks as is the case for NIR spectra.

The curves in FIGS. 6A and B represents set of corresponding dielectric components according to the invention, in this case for a continuous frequency range of 0.1-1.1 THz. If a spectrum is recorded on an unknown mixture, a similar dielectric THz trace can be calculated for the mixture. The calculated trace can be compared the set of traces of FIGS. 6A and B to estimate a concentration in the unknown sample. The comparison may be based on extracted parameters such as mean values, values or inclinations for two or more specific frequencies, or more complicated chemometric methods. Extracted parameter values may be interpolated by a regression model so that a direct reading of the known sample concentration corresponding to the unknown sample concentration can be read from a graph or a table.

Traces similar to those of FIGS. 6A and B where measured for 21 ethanol-water samples of different concentrations. Average values of the absorption coefficient and refractive index where calculated and are presented as the continuous curves in the graphs of FIGS. 7A and B respectively. These curves provide a mapping between the absorption coefficient/refractive index and the ethanol concentration.

Thereafter, spectra were recorded on the following alcoholic beverages, and absorption coefficient/refractive index traces where calculated. These beverages all contain ethanol (the first substance) in a liquid mixture containing water, ethanol and other substances such as sugars, colours flavours and in some cases particles such as yeasts, hop, grape remnants, and gaseous $CO_2$. The composition of the other substances is very different for the different mixtures.

5.8% beer (Thy organic)
   10% beer (Belgium)
   15% Sake (Japan)
   25% Souchu (Japan)
   37.5% Gin (not specified)
   40% Williams pear schnapps (Germany)
   40% Obstwasser (Germany)
   45% Pernod (France)
   47.5% Gin (England)
   55% Red Absinthe (France)
   72% Green Absinthe (Bulgaria)
   85% Green Absinthe (Bulgaria)

Again, average values for each trace where calculated and are shown in the graphs as square points. The size of magnitude indicated inside each square represents the variance in the calculated average value from each trace.

A clear correlation between the ethanol concentration and the THz absorption coefficient/refractive index is seen. The fact that the variation closely follows that of the pure alcohol-water samples means that 1. the other substances have a minor influence on the average value of the THz absorption coefficient/refractive index, and
2. an average value of a dielectric THz trace calculated for an unknown mixture containing other substances can be compared to the values of the pure water/ethanol sample to estimate an ethanol concentration.

In the above example, the set of known samples where pure ethanol/water mixtures. A set of dielectric THz traces can be recorded for a specific type of mixture (e.g. beer or a specific brand of beer) while artificially varying the ethanol concentration by addition of pure ethanol or distilling. Such set of traces with high resolution (e.g. concentration intervals of 1%) in a limited range (e.g. 0-15%) would correspond to the curve in FIGS. 7A and B. By interpolating between values using an optimised regression model, a very precise determination of ethanol content in beer could be made.

Figure 8A:
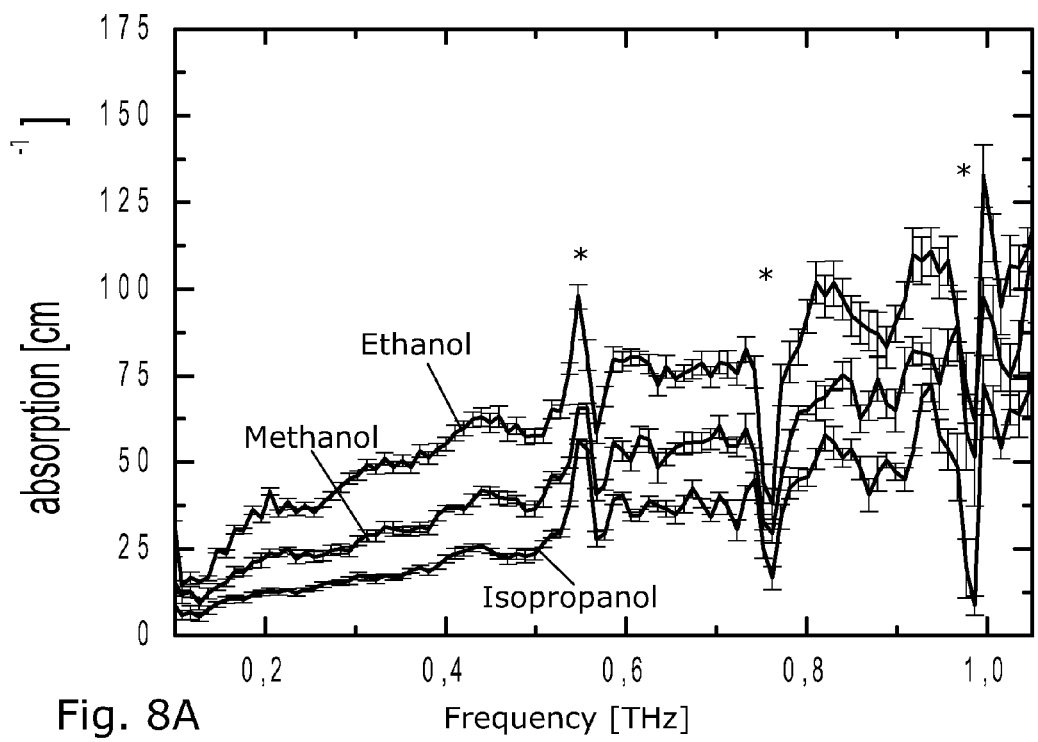
FIGS. 8A and B show dielectric THz traces, absorption coefficient (8A) and index of refraction (8B), for different alcohol-water mixtures.

FIGS. 8A and B show THz absorption coefficient/refractive index traces for different types of pure alcohols; methanol, ethanol and isopropanol. The peaks marked * are caused by atmospheric water vapour in the beam path. The traces are clearly different. A series of traces for different concentrations of ethanol-water and isopropanol-water solutions are recorded, and average values of the THz absorption coefficient/refractive index are calculated and shown in FIGS. 9A and B. It can be seen that the overall behaviour are similar for the two alcohols except at the highest alcohol concentrations where a significant difference is seen.

If the mixture contains two substances which both have pronounced influence on the dielectric THz trace, a set of traces can be recorded for at set on known samples wherein the content of the two (first and second) substances are systematically but independently varied. This will enable a simultaneous determination of the content of both substances in an unknown mixture by comparing the trace of the unknown mixture with the previously recorded traces.

Figure 7A:
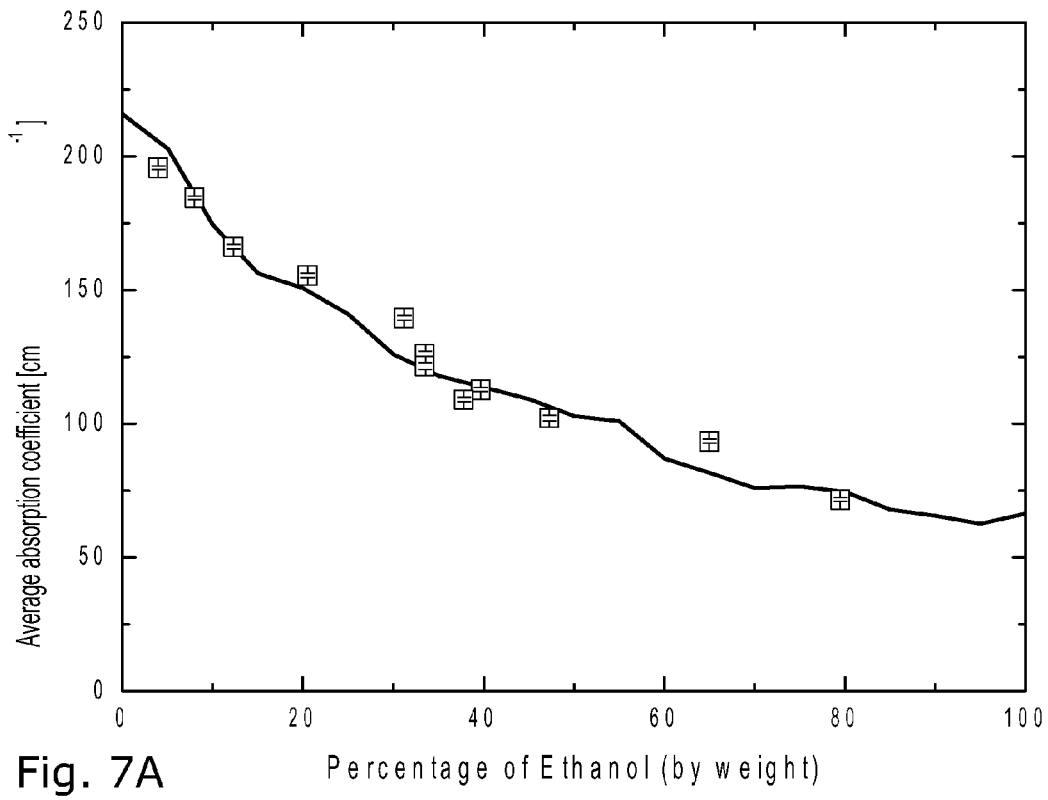
FIGS. 7A and B show average absorption coefficient (7A) and index of refraction (7B) as a function of ethanol concentration for a pure ethanol-water mixture (black line) and a number of beverages (points).
Figure 7B:
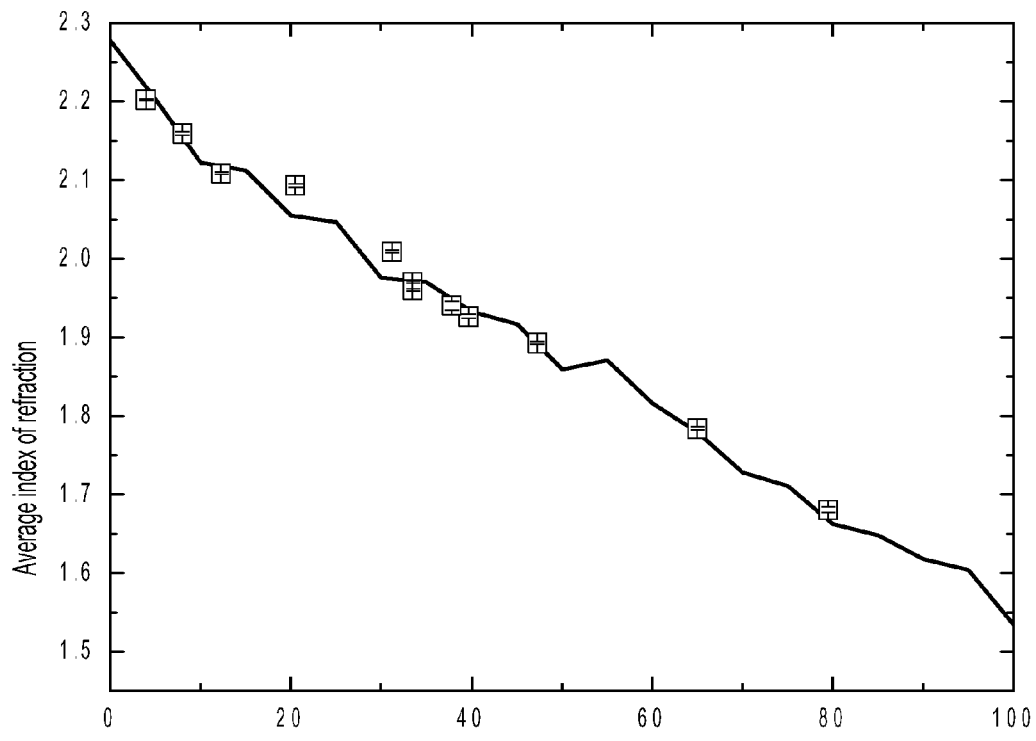
Figure 9A:
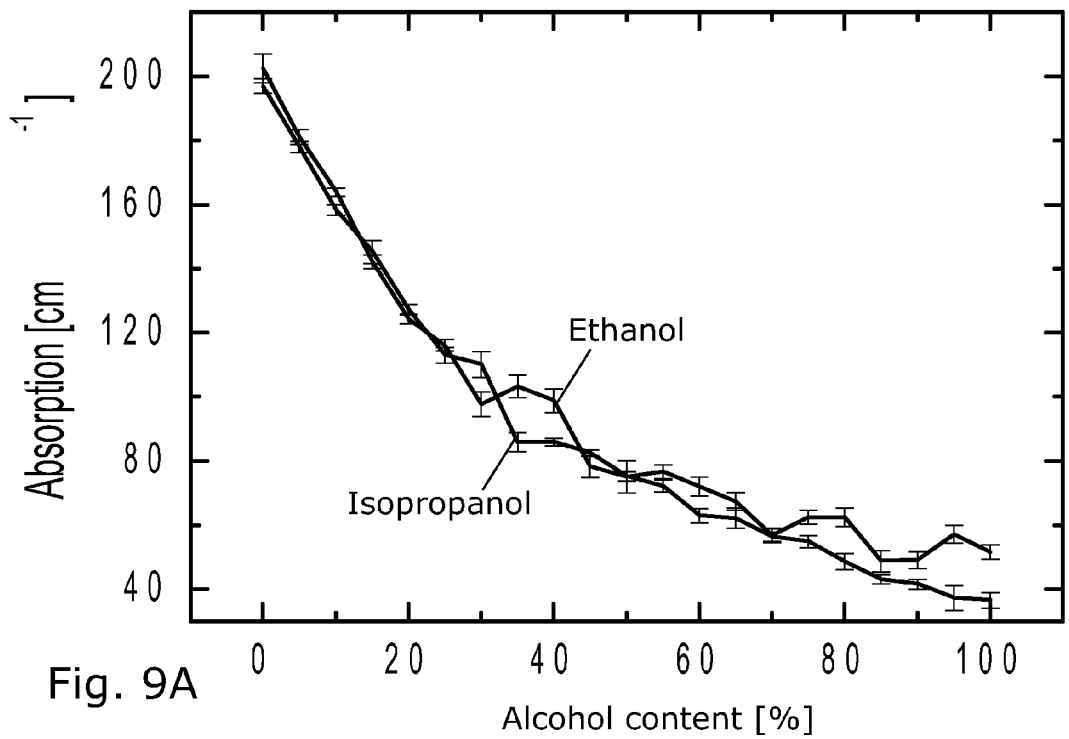
FIGS. 9A and B show average absorption coefficient (9A) and index of refraction (9B) as a function of alcohol concentration for two alcohol-water mixtures.
Figure 9B:
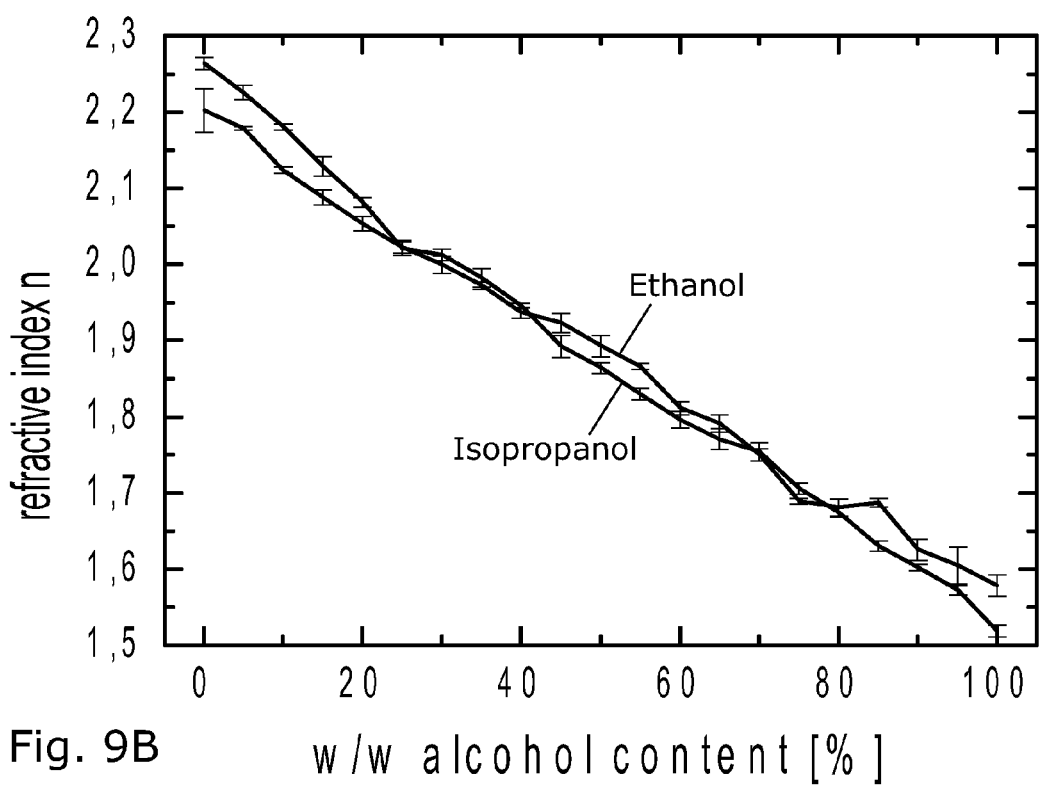
Figure 10A:
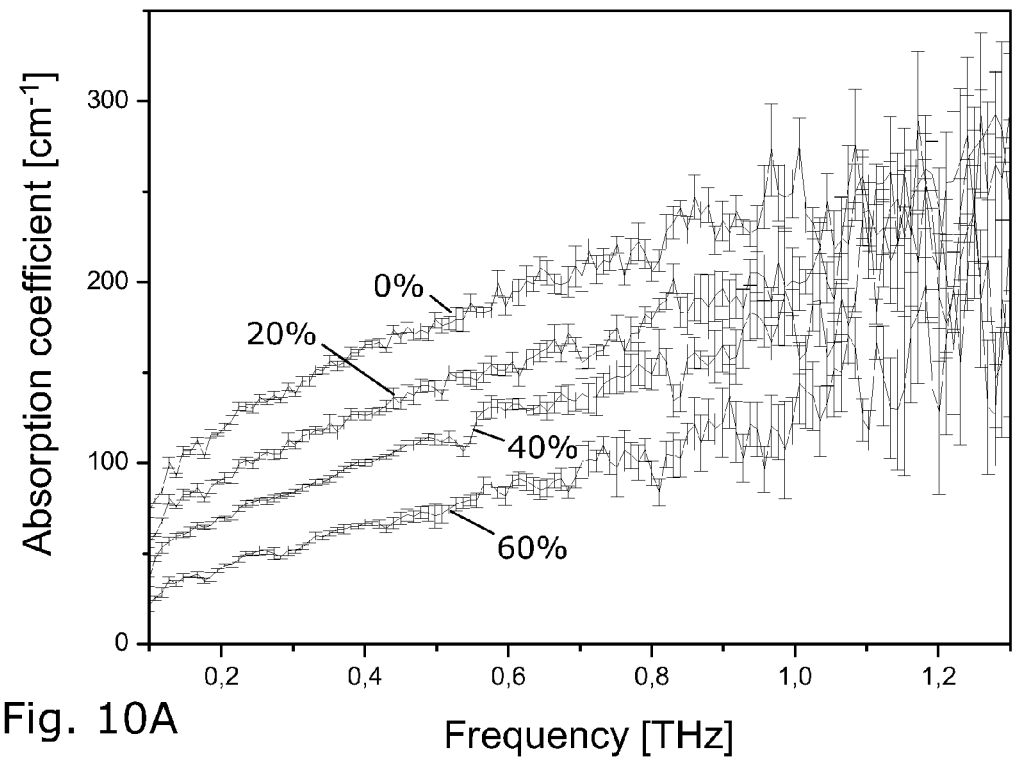
FIG. 10A shows the THz trace for the absorption coefficient for different mixtures of sugar in water.
Figure 10B:
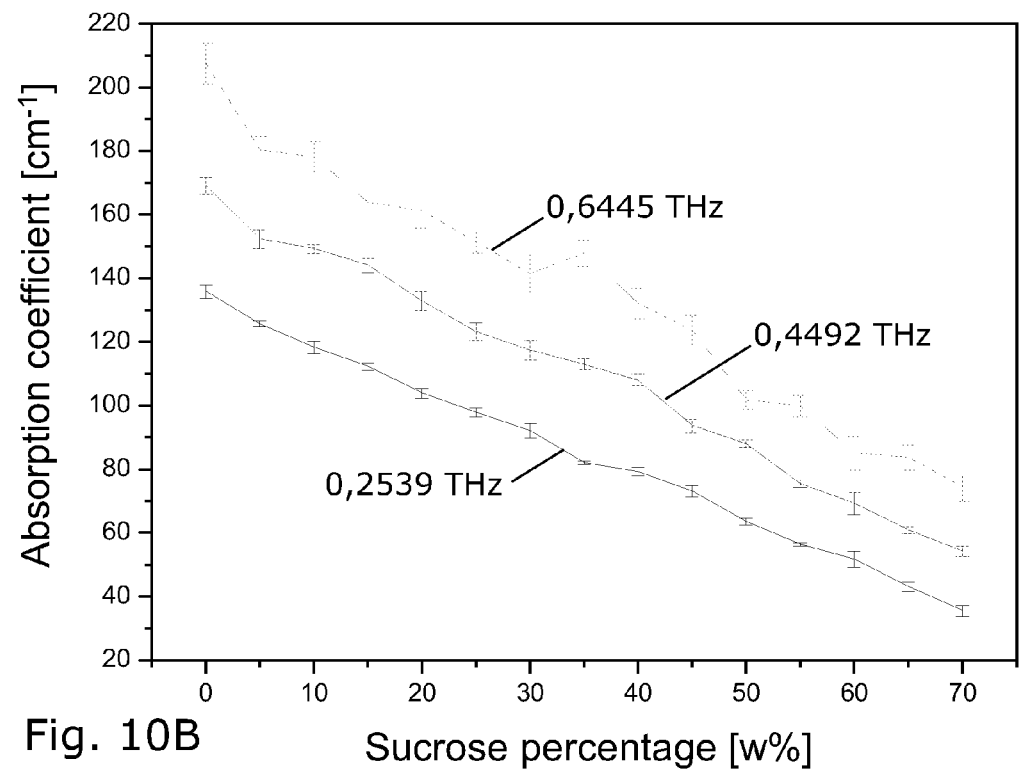
FIG. 10B shows calculated absorption coefficients at selected frequencies (0.25, 0.45, and 0.64 THz) as a function of the content of sugar in the mixtures.

FIG. 10A shows the THz trace for the absorption coefficient for different concentrations of sugar (here sucrose) in water. As in the case of alcohol-water mixtures, the effect of adding sugar to water is pronounced. The dielectric THz traces were determined for a series of different concentrations of sugar-water solutions, and the absorption coefficient at selected frequencies (0.25, 0.45, and 0.64 THz) was calculated as function of the content of sugar in the mixtures, the results are shown in FIG. 10B. Note that the curves in FIG. 10B are show the absorption coefficient at different frequencies, and not an average absorption coefficient over a frequency range in each trace as in the alcohol case (FIGS. 7A and 9A). The reason for this being that the absorption coefficient traces for sugars have much larger inclinations than for alcohols. In a similar manner as the example in FIGS. 7 and 9, it is clear that a regression model is capable of estimating the sugar content of an unknown sugar mixture based on these traces.

The following example illustrates quantitative determination of a substance concentration S in an unknown mixture. Firstly, an average dielectric THz trace is calculated from multiple THz reflection spectroscopic measurements of the mixture. The average trace is formed by adding the dielectric component value for each frequency from the multitude traces.

$$\overline{A}_1 = (A_1^1 + A_1^2 + \ldots + A_1^n)/N$$
$$\vdots$$
$$\overline{A}_m = (A_m^1 + A_m^2 + \ldots + A_m^n)/N$$

Wherein $A_m^n$ is the dielectric component (e.g. absorption coefficient) at frequency m in the n'th trace of the unknown mixture, and N is the number of traces. The average trace is then formed by the series of average dielectric components $\overline{A}_1, \overline{A}_2, \ldots, \overline{A}_m$. A more advanced analysis will use as much spectroscopic information as possible, e.g. both absorption coefficient and index of refraction, in order to increase the accuracy of the estimated substance concentration.

The content Y of the substance in the unknown mixture can then be calculated from $$Y = k_0 + k_1 \cdot \overline{A}_1 + k_2 \cdot \overline{A}_2 + \ldots + k_n \cdot \overline{A}_m,$$

where $k_0, k_1, k_2, \ldots, k_n$ are constants previously determined by a regression model, like partial least square (PLS) and/or principal component analysis (PCA), between dielectric THz traces in the unknown mixture and laboratory analysis data of samples with known concentrations. The regression model is based upon a given number of known samples e.g. 100 samples. The accuracy of PLS, PCA or similar advanced regression methods compared to an estimate based on one or two isolated frequencies depends on the detailed shape of the dielectric component, and is therefore linked to the bandwidth of the THz source and spectrometer; the higher the bandwidth is the more of the full shape of the broad, far-infrared absorption feature of water can be captured by the spectrometer.

Figure 11A:
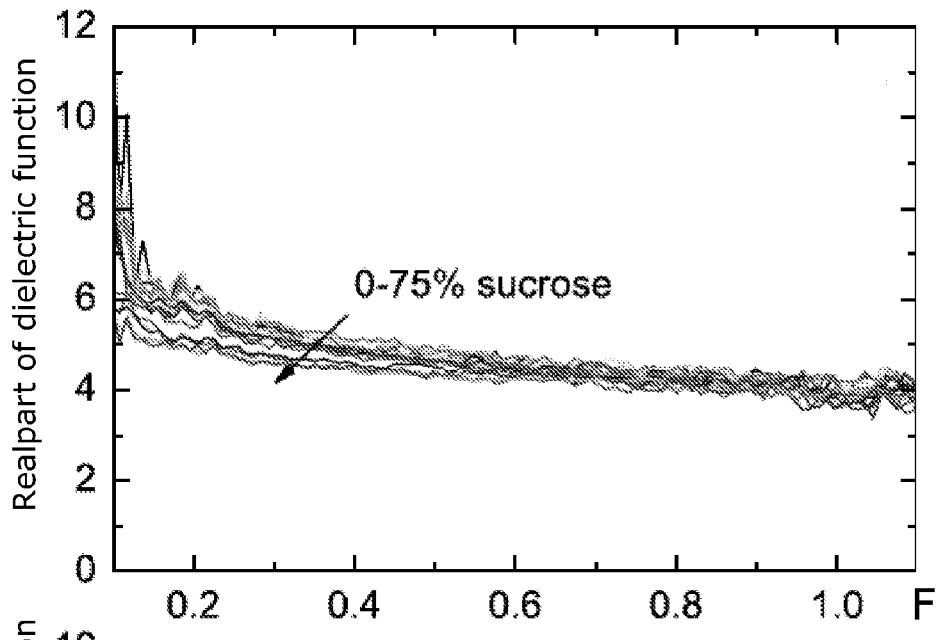
FIGS. 11A-B shows the real and imaginary part of the dielectric function at room temperature of aqueous sucrose solutions, with sucrose concentrations from 0% to 75% by weight, with the arrow pointing to lower values, measured in 5%-intervals.
Figure 11B:
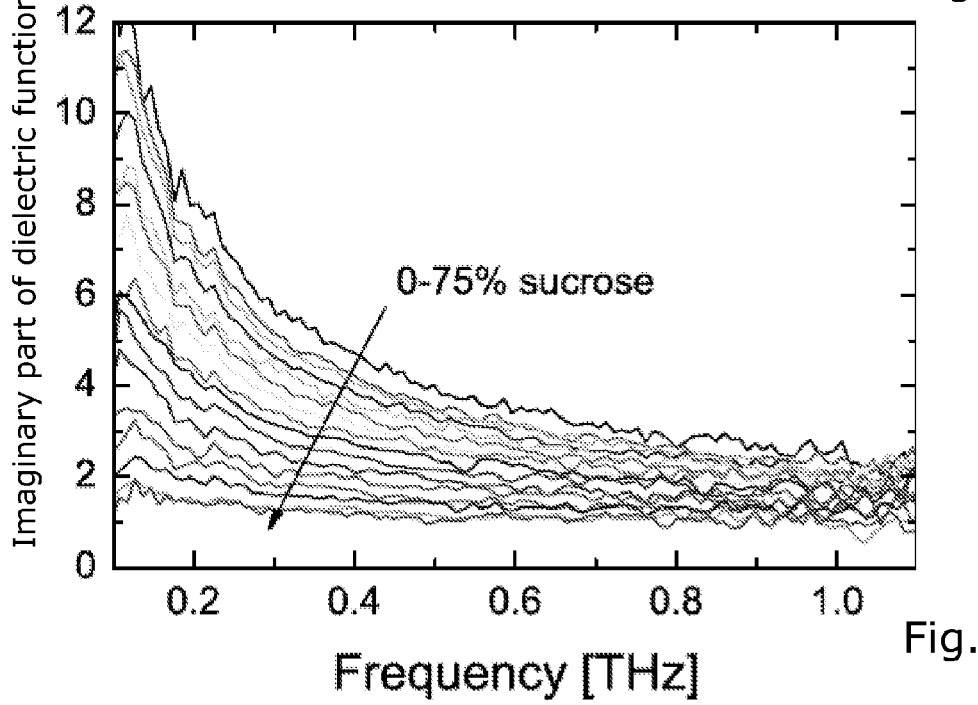
Figure 12:
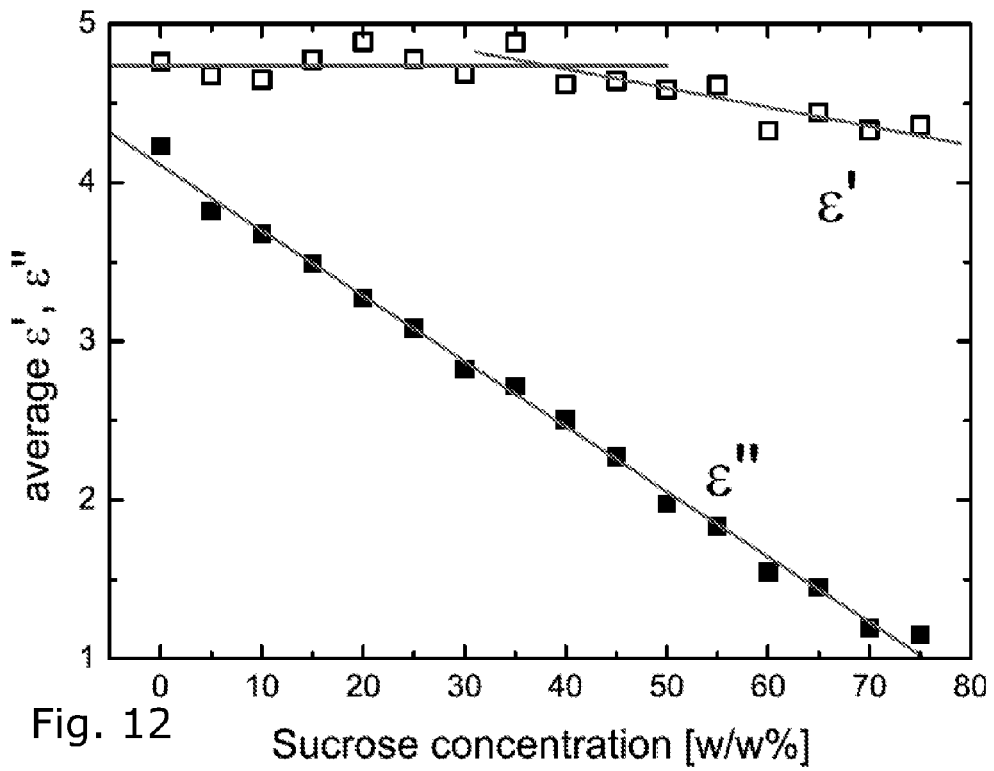
FIG. 12 show the average value of the real and imaginary part, $\epsilon'$ and $\epsilon''$, of the dielectric function in the frequency interval 0.15-1.0 THz of aqueous sucrose solutions as function of the sucrose concentration. The solid curves are phenomenological fits.

In the following, the application of the method and apparatus according to embodiments of the invention for determination of sugar content in the liquid mixture is described, i.e. here the first substance is sucrose. FIGS. 11A and B shows the real part (A) and imaginary part (B) of the dielectric function of aqueous solutions of sucrose, for sucrose concentrations between 0 and 75% by weight, the arrow pointing towards lower concentrations. Preparation of the highest concentrations required a slight heating of the solution in order to dissolve the sucrose, but all measurements are carried out with the sample material at room temperature and without precipitation of sucrose crystals.

The real part of the dielectric function of aqueous solutions of sucrose shows only a weak dependence on the sucrose concentration. The imaginary part of the dielectric function, however, displays a significant dependence on the sucrose concentration. This is in contrast to the effect in ethanol-water mixtures, where a pronounced dependence on the ethanol concentration was observed in both the real and imaginary part of the dielectric function of the solution. The dependence on sucrose concentration of the average dielectric function in the frequency range 0.15-1.0 THz of the sucrose solutions is shown in FIG. 13.

The real part of the dielectric function of the sucrose solutions is seen to be basically independent of the sucrose concentration up to concentrations of approximately 40% by weight. At higher concentrations, a slight decrease of $\varepsilon'0$ is observed. The same plot shows a linear decrease of $\varepsilon'00$ with increasing sucrose concentration. The red curves in FIG. (13) are linear fits to the data, using the functions $$\epsilon'(y) = \begin{cases} D' & y < 40\% \\ E' - F'y & y \geq 40\% \end{cases}$$

$$\epsilon''(y) = E'' - F''y$$

with the fitting parameters D'=4.763±0.032, E''=5.05±0.14, F'=0.00978±0.0024, E''=4.11±0.03, and F'''=0.0415±0.0007.

Thus, by comparing the calculated component(s) with a set of corresponding components determined previously on a set of samples with known concentrations, or a fit determined using such previously determined components, a concentration of the sucrose in the mixture can be estimated.

In the above, it was demonstrated that the dielectric function of an aqueous solution determined by use of methods and apparatus according to embodiments of the invention, is sensitive both to the ethanol content and to the sucrose content. In the following, it is demonstrated that the method and apparatus according to embodiments of the invention can be applied to determine concentrations of both a first and a second substance, here ethanol and sugar, in the liquid mixture.

The basis for this approach is that the modification of the dielectric function of the solution can be described as a sum of the individual modifications arising from the alcohol content and from the sugar content. This assumption may only hold over a limited range of concentrations of alcohol and sugar. However, most commercial beverages and liquors contain a relatively small concentration of sugar.

In FIGS. 13A and B the real and imaginary part of the dielectric function for mixtures of sucrose and ethanol in water are shown together with the dielectric functions of pure water, a water-ethanol solution, and a water-sucrose solution. Clearly the addition of up to 20% sucrose to the pure water as well as to the alcohol solution has little effect on the real part of the dielectric function of the solution. The effect of adding 10 and 20% sucrose to the solutions is clearly seen in as a lowering of the imaginary part of the dielectric function of the solution.

If we denote the ethanol concentration x and the sucrose concentration y, the above analysis indicates that the average dielectric function in the frequency interval 0.15-1.0 THz of a solution of ethanol and sugar in water can be written as $$\epsilon'(x,y) = A' + B' \exp(-C'x)$$

$$\epsilon''(x,y) = A'' + B'' \exp(-C''x) - E''x$$

where the constants in these equations are the same as given earlier. When use this analysis on the dielectric functions of the sucrose-ethanol solutions in FIGS. 13A and B, we obtain a fairly good agreement between the known concentrations of sucrose and ethanol and the concentrations predicted by the model.

Specifically, the 10%-sucrose-20%-ethanol solution was predicted to contain (13.6±2.5) % sucrose and (18.6±1.1) % ethanol. The 20%-sucrose-20%-ethanol solution was predicted to contain (19.4±2.5) % sucrose and (19.4±1.1) % ethanol.

Again, by comparing the calculated components with a set of corresponding components determined previously on a set of samples with known concentrations, or a fit determined using such previously determined components, concentrations of ethanol and sucrose in the mixture can be estimated.

The extraction of the concentration of two components in the solution is possible because both the real and imaginary part of the dielectric function are measured. Two components is the maximum number of components that can be quantified with the method applied here. When applying the method, it is preferable that (a) no other components in the liquid contributes significantly to changes of the dielectric function of the solvent (here water) and (b) that changes of the dielectric function owing to the presence of two components can be described as the sum of the individual contributions.

In the following a method for detecting a volatile liquid or for differentiating between aqueous solutions and volatile liquids with THz reflection spectroscopy is described in accordance with an embodiment of the invention.

The self-referenced reflection technique applied by the present invention can be used to differentiate between (mostly harmless) aqueous solutions and (in some situations critically harmful) volatiles such as fuel, components for liquid explosives, and nonpolar solvents.

It is well established in the field that the polarizability of a dielectric is proportional to the static permittivity, via the relation $$P = \epsilon_0(\epsilon_r - 1)E$$

Polar liquids hence have a high static permittivity $\epsilon_r$, whereas nonpolar liquids have a low static permittivity. The permittivity at THz frequencies is in liquids related to the static permittivity, so there is a direct relation between these two quantities. This means that polar liquids have a high permittivity at THz frequencies whereas nonpolar liquids have a low permittivity at THz frequencies. Examples of the dielectric properties of nonpolar liquids in the THz range are given by Pedersen and Keiding (*THz time-domain spectroscopy of nonpolar liquid*, IEEE Journal of Quantum Electronics 28, 2518, 1992) and examples of the dielectric properties at THz frequencies of polar liquids are given in this disclosure as well as by Kindt and Schmuttenmaer (*Far-infrared dielectric properties of polar liquids probed by femtosecond terahertz pulse spectroscopy*, Journal of Physical Chemistry 100, 10373, 1996). These data clearly shows the distinction between polar and nonpolar liquids.

An important example of a polar liquid is an aqueous solution. The static permittivity of water is 78, and ethanol-water mixtures have slightly lower static permittivities. In contrast, the static permittivity of nonpolar liquids is in general lower than 10, and often lower than 5. This translates to a permittivity of polar liquids in the THz range of 5-10, and a permittivity of nonpolar liquids in the THz range less than 2. Nonpolar liquids with low viscosities (close to that of water) are in general highly volatile and flammable.

Most transparent plastics (PET, PC, etc) have similar dielectric permittivities in the THz range. Hence the reflection coefficient of a THz field reflected at a plastic-liquid interface, $$r = \frac{1 - n_{liq}/n_{plast}}{1 + n_{liq}/n_{plast}},$$

will be very low for nonpolar liquids, and significant for polar liquids. This means that liquids with an index close to that of the plastic (around 1.5-1.6) will give a weak return signal, whereas high-index liquids, such as strongly hydrogen-bonded liquids, will lead to a strong return signal.

Hence a reflection measurement in the THz range can be used for detecting volatile liquids or for distincting between polar and nonpolar liquids through plastic walls, such as PET bottles. The same argument holds for measurements through glasses with similar dielectric properties in the THz range as plastics.

Figure 14:
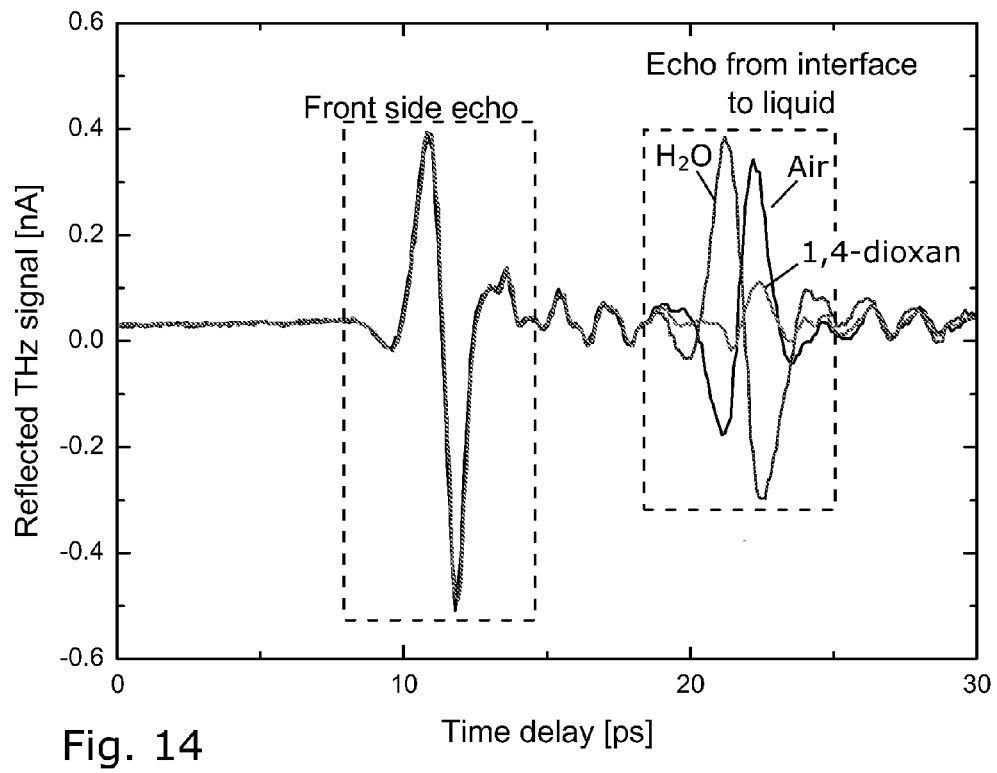
FIG. 14 shows THz return signals from a 1-mm plastic wall with different liquids behind.

An example of such detections or distinction is described in the following in relation to FIG. 14, showing the return signal from the plastic interface of the same container with different liquids. The signals are recorded with the THz optics at 10 cm stand-off distance from the plastic wall. The three traces show the return signal with air at the back side of the plastic, water, and the flammable liquid 1,4-dioxan. Whereas the return signal from the front surface of the window is always the same, the return signal from the interface between plastic and the liquid is strongly dependent on the nature of the liquid. The return signal is much stronger from water than from the flammable liquid because of the much different dielectric properties of the two types of liquids as explained in the above.

Hence the return signal is a measure of the nature of the liquid: hydrogen-bonded or non-hydrogen-bonded. In practice, as elaborated in the above, these two classes of liquids correspond to water-based liquids and volatile (and hence flammable, dangerous) liquids. Thus, by comparing the component(s) calculated from the reflected THz signal to a predetermined value, it can be determined if the liquid is potentially volatile. Such component(s) and value may typically be permittivities or reflection coefficients at the relevant THz frequencies.

17. The method according to claim 16, wherein the step of comparing the calculated component(s) comprises comparing the calculated component(s) with a set of corresponding components being previously recorded and calculated for said at least two frequencies using the above steps on a set of volatile liquid samples, thereby estimating a degree of hydrogen-bonding of the liquid.

Figure 15:
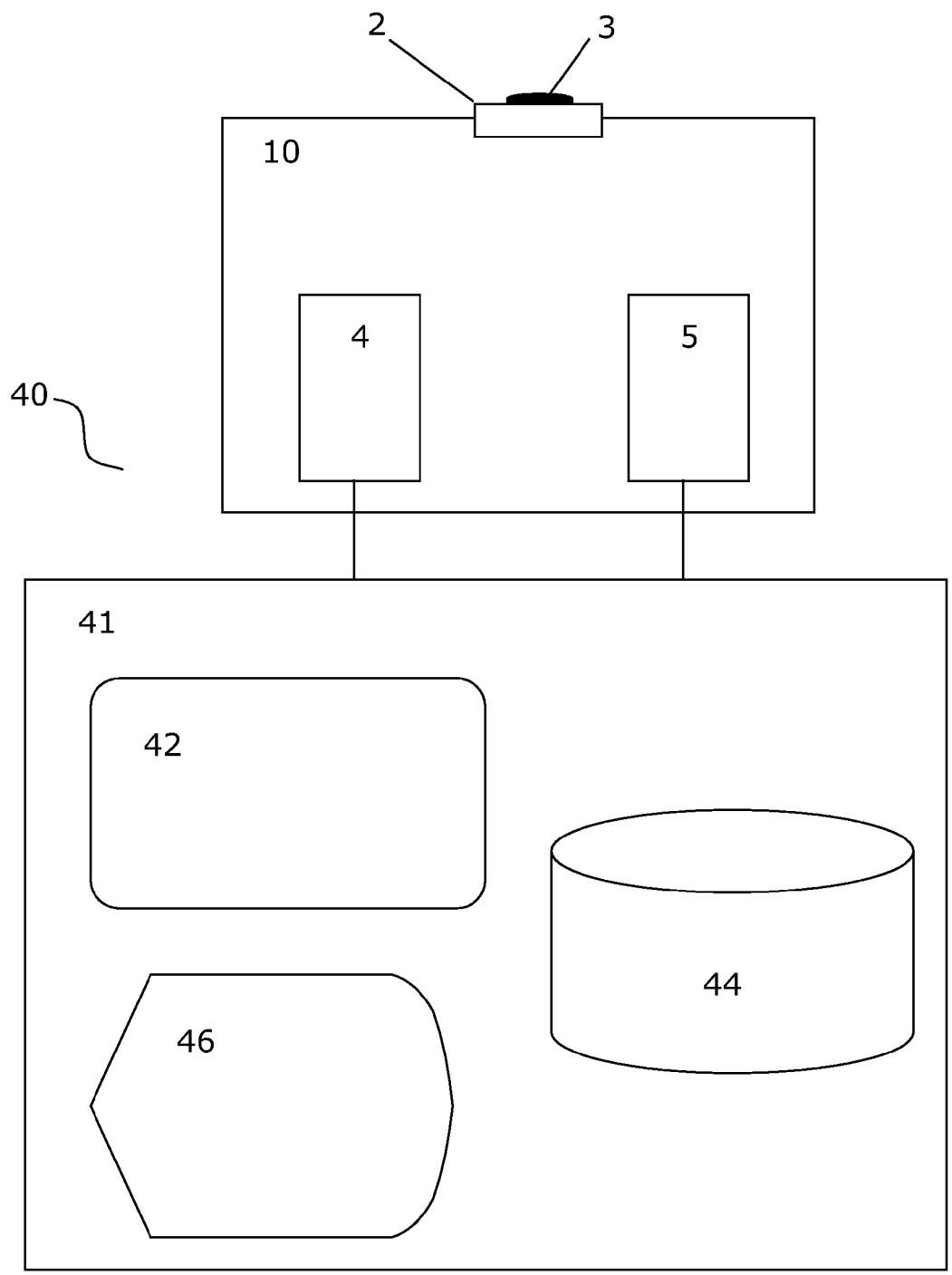
FIG. 15 illustrates an apparatus 40 for optically determining a concentration of substances in a mixture, or detecting volatile liquids, based on reflection THz spectrometry. The appraratus comprises a reflection THz spectrometry arrangement 10 as described in relation to FIG. 1, comprising window section 2 for positioning of sample 3 and THz source 4 and THz spectrometer 5. The THz source 4 and THz spectrometer 5 are connected to a data processing unit 41 comprising a processor 42, storage 44 and output means 46 such as a display, a printer or a transmission unit for sending data.
Figure 8A:
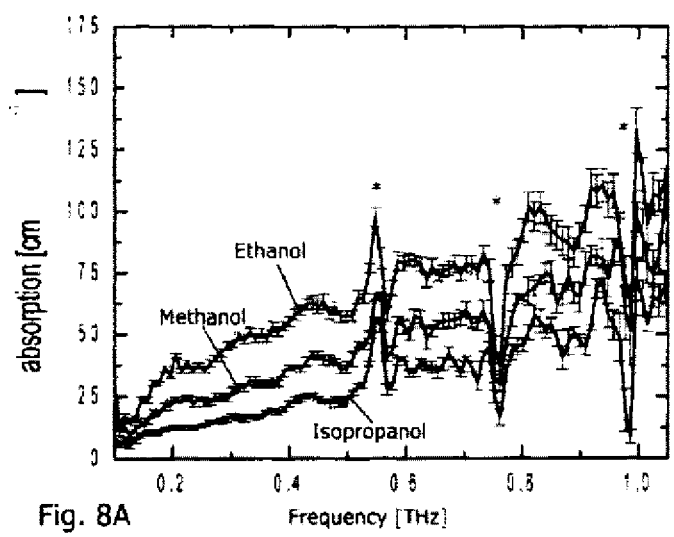
Figure 8B:
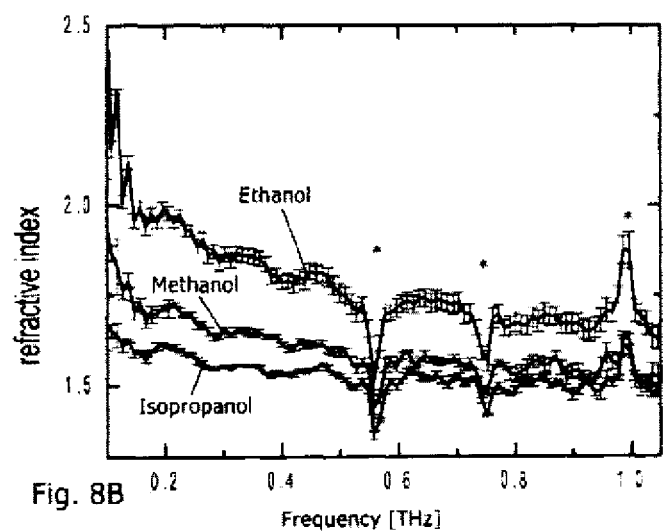

FIG. 15 illustrates an apparatus 40 for optically determining a concentration of substances in a mixture, or detecting volatile liquids, based on reflection THz spectrometry. The apparatus comprises a reflection THz spectrometry arrangement 10 as described in relation to FIG. 1, comprising window section 2 for positioning of sample 3 and THz source 4 and THz spectrometer 5. The THz source 4 and THz spectrometer 5 are connected to a data processing unit 41 comprising a processor 42, storage 44 and possibly output means 46 such as a display, a printer or a transmission unit for sending data.

The data processing unit 41 is typically a computer or equivalent. The data processing unit can control the recording of spectra and receive recorded spectra. Processor 42 and storage 44 can process received spectra and thereby implement the various calculating and comparing means according to the invention. The various calculating and comparing means is preferably software for performing the data analysis described previously, which software is held by the storage and executed by the processor. The storage is further adapted to hold the previously recorded and calculated set of dielectric THz traces used in the comparing and estimation procedure.

The invention claimed is:

1. A method for determining a concentration of a first substance in a liquid mixture containing water, the first substance and other substances, the method applies self-referenced reflection THz spectroscopy and comprises:

on a section of a plane window of thickness d and refractive index $n_{win}$ having a front and a back side, providing the mixture in contact with the back side;

irradiating coherent THz radiation with frequencies within the range 0.05-2 THz on the front of the window section at an angle of incidence θ, the incident radiation resulting in a reference signal reflected from the front of the window section and a sample signal reflected from the back side of the window section;

recording the reference and sample signals in the time domain;

calculating by a processor at least one component of the complex index of refraction of the mixture $\hat{n}_{mix}(\omega)$ or the complex reflection coefficient $\hat{r}_{win/mix}(\omega)$, each of the at least one component being determined for at least two frequencies in said range; and comparing the calculated component(s) with a set of corresponding components being previously recorded and calculated for said at least two frequencies using the above steps on a set of samples with known concentrations of the first substance in water, thereby estimating a concentration of the first substance in the mixture.

2. The method according to claim 1, wherein:
the incident coherent THz radiation is broadband pulses, so that the reference and sample signals are corresponding pulses with corresponding bandwidths;
the step of recording the reference and sample signals comprises recording the signal strength of the reference and sample pulses, $\hat{E}_{ref}(t)$ and $\hat{E}_{sam}(t)$, and determining a difference in arrival time between reference and sample pulses originating from the same incident pulse; and
the step of calculating at least one component comprises determining a relative amplitude of and a phase shift between the reference and sample signals in the frequency domain, $$\frac{\hat{E}_{sam}(\omega)}{\hat{E}_{ref}(\omega)} = A_m^{new} \exp(i\Delta_m^{new}).$$

3. The method according to claim 2, wherein the step of calculating at least one component of $\hat{n}_{mix}(\omega)$ or $\hat{r}_{win/mix}(\omega)$ applies an expression of the form $$\hat{r}_{win/mix}(\omega) = \frac{A_m^{new}}{A_m^{ref}} r_{win/air} \exp(i(\Delta_m^{new} - \Delta_m^{ref}))$$

or $$\hat{n}_{mix}(\omega) = \frac{\sqrt{n_{win}^2(1-\hat{r}_{win/mix})^2 + 4\hat{r}_{win/mix}\sin^2\theta}}{1+\hat{r}_{win/mix}},$$

where $A_m^{ref}$ and $\Delta_m^{ref}$ are relative amplitude and phase measured previously measured without air on the back side of the window section and $r_{win/air}$ is the reflection coefficient with air on the back side of the window section.

4. The method according to claim 3, further comprising determining the previously measured relative amplitude and phase, $A_m^{ref}$ and $\Delta_m^{ref}$, once for each combination of d, $n_{win}$ and θ, by performing the above steps without a mixture in contact with the back side of the window section.

5. The method according claim 2, wherein the broadband THz pulses have a bandwidth covering at least 0.1-1 THz.

6. The method according to claim 1, wherein:
the incident coherent THz radiation comprises two or more discrete (CW) frequencies within a range of 0.1-1.5 THz, so that the reference and sample signals forms an interference signal;
the step of recording the reference and sample signals comprises recording, for each of the two or more discrete frequencies, an amplitude and a phase of said interference signal, $A_i^{new}\exp(i\Delta_i^{new}) = \hat{E}_{sam}(\omega) + \hat{E}_{ref}(\omega)$; and
the step of calculating at least one component comprises determining a difference between said interference signal and a similar interference signal previously recorded without a mixture in contact with the back side of the window section.

7. The method according to claim 6, wherein the two or more discrete frequencies are selected to coincide with a frequency where said interference signal have a minimum or a maximum.

8. The method according to claim 6, wherein the two or more discrete (CW) frequencies comprises at least one frequency within the range 0.05-0.2 THz.

9. The method according to claim 1, wherein the mixture is a water-based emulsion, comprises suspended particles and/or comprises dissolved and gaseous carbon dioxide.

10. The method according to claim 1, wherein the first substance is one of: alcohols such as methanol, ethanol or propanol, acetone, sugars such as sucrose, glucose or fructose, acids, fatty acids, salts, urea.

11. The method according to claim 1, wherein the other substances comprise one or more of: sugars, yeasts, fermentative products, colours, gaseous carbon dioxide, suspended particles, and fat globules.

12. The method according to claim 1, wherein the volume of mixture provided at the back side of the window section is less than 1 μL, such as less than 0,1 μL, such as less than 20 nL.

13. The method according to claim 1, wherein the other substances comprise a second substance and the samples with known concentrations have varying concentrations of said second substance, and wherein the step of comparing the calculated component(s) estimates concentrations of both the first and the second substance in the mixture.

14. The method according to claim 1, wherein the comparing and estimating are performed by multivariate analysis.

15. An apparatus for optically determining a concentration of a substance in a liquid mixture containing water, the first substance and other substances, the apparatus comprising:
a reflection THz spectrometer comprising a source of THz radiation of frequency within a range of 0.05-2 THz and a THz time domain detector;
a plane window section of thickness d and refractive index $n_{win}$ having a front and a back side, the back side being adapted to be in contact with the liquid mixture, the window section being positioned to receive THz radiation on the front of the window section at an angle of incidence θ from the source, and so that a reference signal being a reflection of the incident radiation on the front of the window section and a sample signal reflected being a reflection of the incident radiation on the back side of the window section can be detected by the THz time domain detector;
a data processing unit comprising:
means calculating at least one component of the complex index of refraction of the mixture, $\hat{n}_{mix}(\omega)$, or the complex reflection coefficient, $\hat{r}_{win/mix}(\omega)$, based on signals detected by the THz time domain detector, each of the at least one component being determined for at least two frequencies in said range;

storage means holding a set of corresponding components being previously recorded and calculated for said at least two frequencies using the above steps on a set of known concentrations of the first substance in water;

means for comparing the calculated component(s) with the set of previously recorded corresponding components to estimate a concentration of the first substance in the mixture.

16. A method for detecting volatile liquids in closed containers, the method applies self-referenced reflection THz spectroscopy and comprises:

providing a container holding a liquid, a section of the container being transparent to THz electromagnetic radiation, having thickness d and refractive index $n_{win}$ and a front and a back side, where the liquid is in contact with the back side:

irradiating coherent THz radiation with frequencies within the range 0.05-2 THz on the front of the window section at an angle of incidence θ, the incident radiation resulting in a reference signal reflected from the front of the window section and a sample signal reflected from the back side of the window section; recording the reference and sample signals in the time domain;

analysing by a processor at least the sample signal reflected from the back side of the window section to determine if the liquid is volatile.

17. The method according to claim 16, wherein the analysis of the sample signal comprises comparing the signal strength and/or shape to previously recorded signals from known liquids.

18. The method according to claim 16, further comprising:

calculating at least one component of the complex index of refraction of the mixture $\hat{n}_{mix}(\omega)$ or the complex reflection coefficient $\hat{r}_{win/mix}(\omega)$, each of the at least one component being determined for at least two frequencies in said range; and comparing the calculated component(s) to a predetermined threshold value to determine if the liquid is volatile.

19. The method according to claim 18, wherein the step of comparing the calculated component(s) comprises comparing the calculated component(s) with a set of corresponding components being previously recorded and calculated for said at least two frequencies using the above steps on a set of volatile liquid samples, thereby estimating a degree of hydrogen-bonding of the liquid.

* * * * *

UNITED STATES PATENT AND TRADEMARK OFFICE
CERTIFICATE OF CORRECTION

PATENT NO.         : 8,374,800 B2                                  Page 1 of 6
APPLICATION NO.    : 12/305612
DATED              : February 12, 2013
INVENTOR(S)        : Jepsen It is certified that error appears in the above-identified patent and that said Letters Patent is hereby corrected as shown below:

On the Title Page

In column 1, (page 2 item 56) at line 9, Under Other Publications, change "infared" to --infrared--.

Signed and Sealed this
Eleventh Day of March, 2014

Michelle K. Lee
*Deputy Director of the United States Patent and Trademark Office*

Figure 8B:
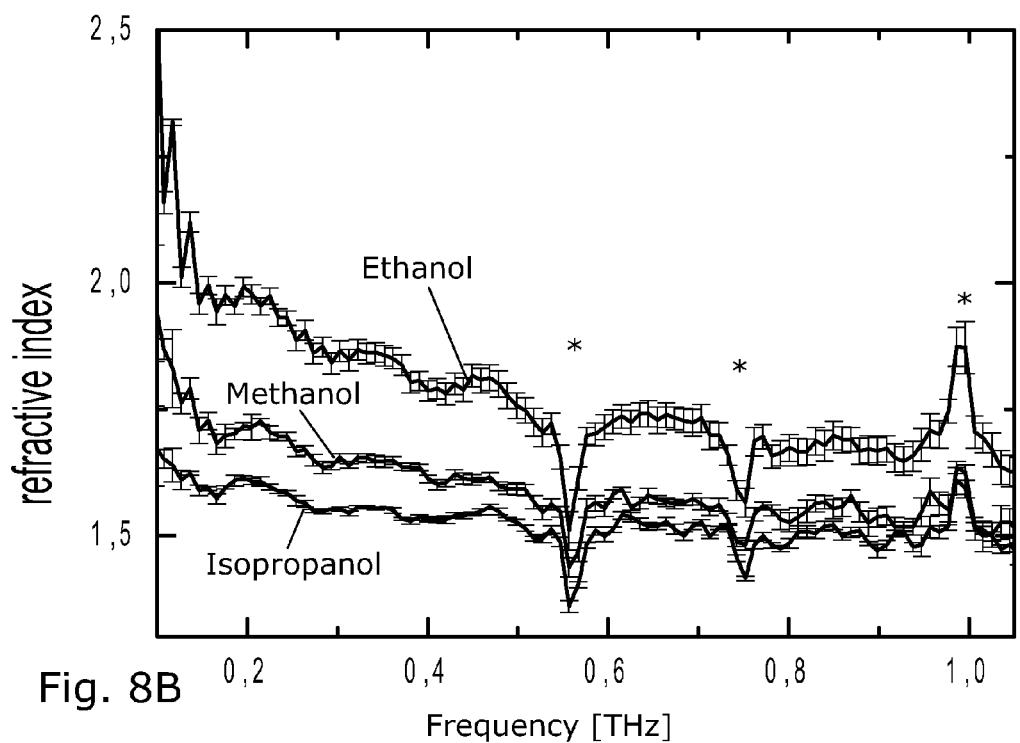

In the Drawings
Sheet 7 of 13 (FIG. 8A and 8B) at line 1-14, (approx.), Change
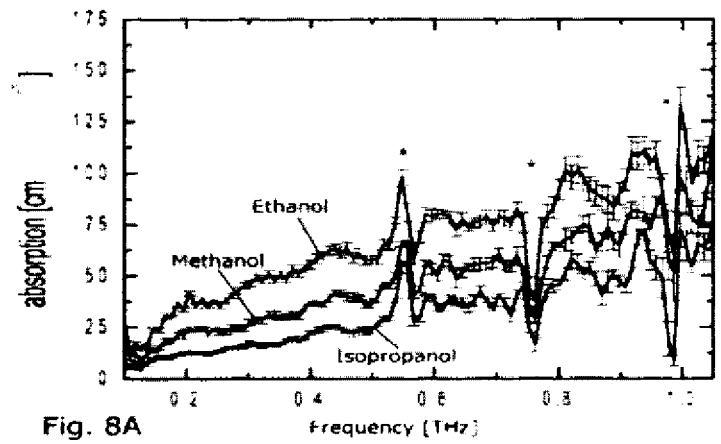
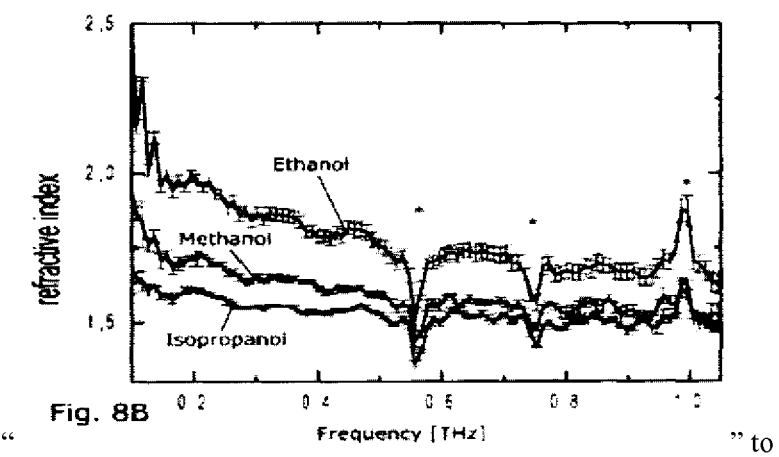
" to Sheet 8 of 13 (FIG. 9B) at line 1-10 (approx.), Change
"  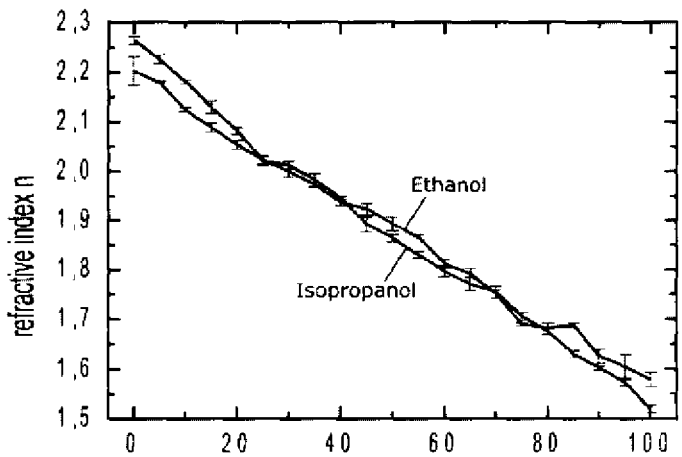 " to
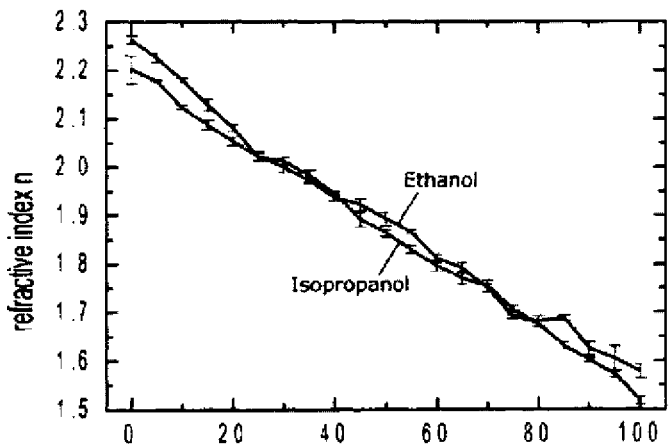
Sheet 9 of 13 (FIG. 10A) at lines 1-7 (approx.), Change
"  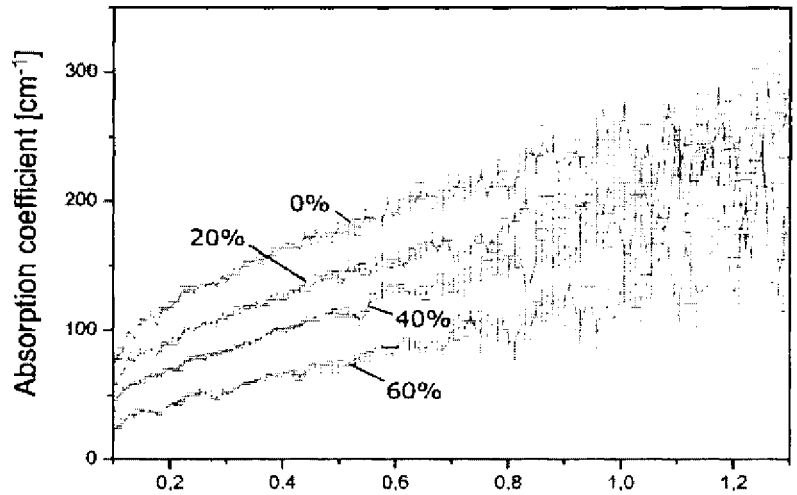 " to

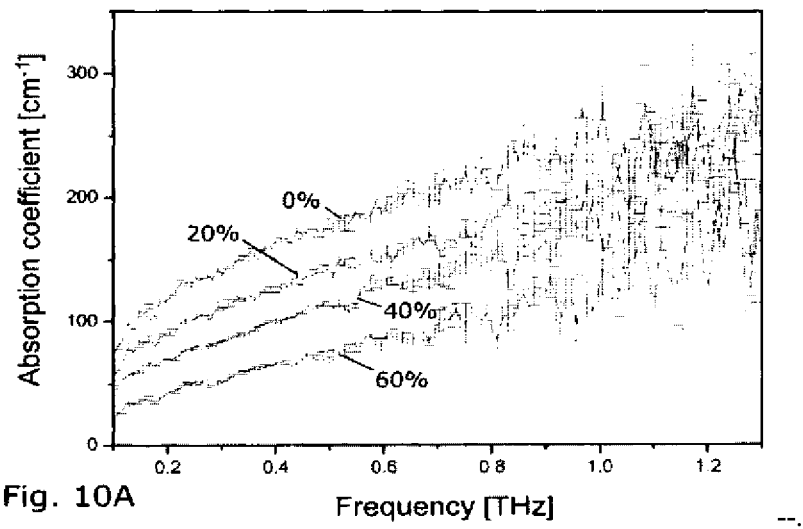

Fig. 10A

Sheet 9 of 13 (FIG. 10B) at line 4 (approx.), Change "0,6445" to --0.6445--.

Sheet 9 of 13 (FIG. 10B) at line 6 (approx.), Change "0,4492" to --0.4492--.

Sheet 9 of 13 (FIG. 10B) at line 8 (approx.), Change "0,2539" to --0.2539--.

In the Specifications

In column 1 at line 18, Change "On" to --on--.

In column 3 at line 58, Change "]0.25;" to --[0.25;--.

In column 3 at line 60, Change "]0.15;" to --[0.15;--.

In column 3 at line 60, Change "]0.4;" to --[0.4;--.

In column 8 at line 13, Change "appraratus" to --apparatus--.

In column 9 at line 5, Change "femtoseond" to --femtosecond--.

In column 11 at line 6, Change "$\frac{E_{sam}}{E_{ref}} = A_m^{ref} \exp(i\Delta_m^{ref}) = \frac{t_{12} r_{23,air} t_{21}}{t_{12}} \exp(2 i n_{Si} d_{eff} \omega/c) A \exp(i\Delta)$" to "$\frac{E_{sam}}{E_{ref}} = A_m^{ref} \exp(i\Delta_m^{ref}) = \frac{t_{12} r_{23,air} t_{21}}{t_{12}} \exp(2 i n_{Si} d_{eff} \omega/c) A \exp(i\Delta)$" --.

In column 11 at line 62, Change "$A_m^* \exp(i\Delta_m^*) = \hat{r}_{23,sample} \frac{t_{12} t_{21}}{r_{12}} \exp(2 i n_{Si} d_{eff} \omega/c)$" to "$A_m^* \exp(i\Delta_m^*) = \hat{r}_{23,sample} \frac{t_{12} t_{21}}{r_{12}} \exp(2 i n_{Si} d_{eff} \omega/c)$" --.

In column 12 at line 2, Change "$\hat{r}_{23,sample} = A_m^* \exp(i\Delta_m^*) \cdot \frac{r_{12}}{t_{12} t_{21}} \exp(-2 i n_{Si} d_{eff} \omega/c)$" to $$\hat{r}_{23,sample} = A_m^* \exp(i\Delta_m^{'}) \cdot \frac{r_{12}}{t_{12}t_{21}} \exp(-2i n_{Si} d_{eff} \omega/c)$$

In column 12 at line 44, Change "of" to --5 of--.

In the Claims

In column 21 at line 66, In Claim 5, Change "according claim" to --according to claim--.

In column 22 at line 36, In Claim 12, Change "0,1" to --0.1--.